(12) United States Patent
Luke

(10) Patent No.: US 10,859,575 B2
(45) Date of Patent: Dec. 8, 2020

(54) MYCOBACTERIUM TUBERCULOSIS SPECIFIC PEPTIDES FOR DETECTION OF INFECTION OR IMMUNIZATION IN NON-HUMAN PRIMATES

(71) Applicant: Intuitive Biosciences, Inc., Middleton, WI (US)

(72) Inventor: Kimberly Luke, Madison, WI (US)

(73) Assignee: Intuitive Biosciences, Inc., Middleton, WI (US)

( * ) Notice: Subject to any disclaimer, the term of this patent is extended or adjusted under 35 U.S.C. 154(b) by 0 days.

(21) Appl. No.: 16/154,054

(22) Filed: Oct. 8, 2018

(65) Prior Publication Data

US 2019/0025302 A1    Jan. 24, 2019

Related U.S. Application Data

(63) Continuation of application No. 15/212,478, filed on Jul. 18, 2016, now Pat. No. 10,094,830, which is a continuation of application No. 14/373,286, filed as application No. PCT/US2013/025072 on Feb. 7, 2013, now Pat. No. 9,404,923.

(60) Provisional application No. 61/595,805, filed on Feb. 7, 2012, provisional application No. 61/723,094, filed on Nov. 6, 2012.

(51) Int. Cl.
*G01N 33/53* (2006.01)
*G01N 33/569* (2006.01)
*G01N 33/543* (2006.01)
*C07K 14/35* (2006.01)

(52) U.S. Cl.
CPC ......... *G01N 33/5695* (2013.01); *C07K 14/35* (2013.01); *G01N 33/54366* (2013.01); *G01N 33/54386* (2013.01); *G01N 2469/20* (2013.01)

(58) Field of Classification Search
CPC .................................................... G01N 33/53
See application file for complete search history.

(56) References Cited

U.S. PATENT DOCUMENTS

| 6,436,409 | B1  | 8/2002  | Gicquel et al. |
| 6,555,653 | B2* | 4/2003  | Alderson ............... C07K 14/35 530/350 |
| 7,311,922 | B1* | 12/2007 | Skeiky .................. A61K 39/04 424/130.1 |
| 7,709,211 | B2  | 5/2010  | Gennaro |
| 2005/0272104 | A1 | 12/2005 | Chan et al. |
| 2006/0057621 | A1 | 3/2006  | Lyashchenko |
| 2009/0011426 | A1 | 1/2009  | Mackintosh et al. |
| 2009/0053258 | A1 | 2/2009  | Olwill et al. |
| 2009/0280140 | A1 | 11/2009 | Laal et al. |
| 2010/0129391 | A1 | 5/2010  | Reed et al. |
| 2011/0236411 | A1* | 9/2011 | Scholler ............. A61K 39/0011 424/193.1 |

FOREIGN PATENT DOCUMENTS

| CN | 101477125 | 7/2009 |
| CN | 101735321 | 6/2010 |
| EP | 1712629 | 10/2006 |
| WO | 97/09429 | 3/1997 |
| WO | 01/98460 | 12/2001 |
| WO | 2006/117538 | 11/2006 |
| WO | WO-2009039854 A2 * | 4/2009 ............ A61K 39/12 |
| WO | 2011/045612 | 4/2011 |
| WO | 2011/135369 | 11/2011 |
| WO | 2012/057904 | 5/2012 |

OTHER PUBLICATIONS

Kanaujia et al., "Recognition of ESAT-6 sequences by antibodies in sera of tuberculous nonhuman primates," Clinical and Diagnostic Laboratory Immunology, vol. 11, No. 1, pp. 222-226 (Jan. 2004).
Supplementary Partial EP Search Report, EP Patent Application No. 13746026.7 dated Oct. 21, 2015.
Supplementary EP Search Report, EP Patent Application No. 13746026.7 dated Feb. 22, 2016.

* cited by examiner

*Primary Examiner* — Albert M Navarro
(74) *Attorney, Agent, or Firm* — Casimir Jones S.C.; J. Mitchell Jones

(57) ABSTRACT

The present invention relates to novel peptides that may be used in whole or in combination for the detection of *Mycobacterium tuberculosis* infection. In particular, the present invention relates to compositions and methods involving detection of antibodies contained in the blood of non-human primates that arise from an infection from *M. tuberculosis* or vaccination using an epitope specific inoculation. More particularly, the present invention provides a means to distinguish early, active, and latent *M. tuberculosis* infection. More particularly, the present invention describes an immunological diagnostic mechanism for the detection of *M. tuberculosis* infection.

2 Claims, 2 Drawing Sheets

Specification includes a Sequence Listing.

Figure 3

| Disease State | Naive | Early | | | | | Active | | | Latent | | | |
|---|---|---|---|---|---|---|---|---|---|---|---|---|---|
| Infection Type | Exper. | Experimental | | | | | Experimental | | | Natural | Experimental | | |
| Mix (6, 15, 17, 20) | 7742 | 14864 | 12929 | 23098 | 17542 | 22925 | 21604 | 15813 | 25131 | 17373 | 15767 | 38889 | 26488 |
| Peptide 1 | 2818 | 2976 | 2615 | 14243 | 3334 | 3656 | 2729 | 2323 | 3942 | 3768 | 4348 | - | - |
| Peptide 2 | 1835 | 2090 | 1936 | 10500 | 1992 | 2391 | 1880 | 2041 | 3139 | 7161 | 2787 | - | - |
| Peptide 3 | 2531 | 5347 | 2100 | 13355 | 2368 | 2401 | 1912 | 11952 | 27204 | 660 | 8236 | - | - |
| Peptide 4 | 665 | 364 | 715 | 770 | 372 | 577 | 900 | 589 | 1759 | 4153 | 1185 | - | - |
| Peptide 5 | 539 | 327 | 696 | 511 | 301 | 519 | 752 | 429 | 1269 | 760 | 1043 | - | - |
| Peptide 6 | 792 | 494 | 763 | 1737 | 795 | 870 | 924 | 581 | 2526 | 556 | 2184 | - | - |
| Peptide 7 | 608 | 462 | 543 | 548 | 277 | 485 | 724 | 355 | 1094 | 1683 | 958 | - | - |
| Peptide 8 | 984 | 727 | 1141 | 9900 | 1954 | 1590 | 1094 | 777 | 2456 | 424 | 1533 | - | - |
| Peptide 9 | 1922 | 2050 | 1926 | 5578 | 2266 | 2922 | 2427 | 12226 | 14104 | 560 | 4131 | - | - |
| Peptide 10 | 670 | 503 | 755 | 575 | 335 | 563 | 853 | 484 | 1389 | 3967 | 1171 | - | - |
| Peptide 11 | 717 | 522 | 1196 | 434 | 865 | 657 | 792 | 698 | 1356 | 543 | 1145 | - | - |
| Peptide 12 | 620 | 528 | 744 | 511 | 358 | 509 | 852 | 428 | 1331 | 479 | 1101 | - | - |
| Peptide 13 | 568 | 487 | 754 | 455 | 315 | 459 | 777 | 468 | 1249 | 1776 | 859 | - | - |
| Peptide 14 | 1086 | 2442 | 1917 | 3751 | 892 | 1349 | 1519 | 1075 | 1920 | 571 | 3520 | - | - |
| Peptide 15 | 1032 | 5131 | 1153 | 2710 | 6961 | 5378 | 1994 | 1670 | 14918 | 578 | 7199 | - | - |
| Peptide 16 | 659 | 676 | 809 | 641 | 368 | 543 | 934 | 457 | 1372 | 3541 | 1176 | - | - |
| Peptide 17 | 2199 | 1561 | 2491 | 8086 | 1069 | 2544 | 1745 | 2349 | 3152 | 620 | 2530 | - | - |
| Peptide 18 | 705 | 781 | 778 | 679 | 399 | 493 | 951 | 445 | 1282 | 2182 | 1093 | - | - |
| Peptide 19 | 767 | 711 | 906 | 573 | 361 | 515 | 993 | 511 | 1376 | 7407 | 1177 | - | - |
| Peptide 20 | 3382 | 4316 | 3404 | 12179 | 3376 | 3356 | 4715 | 4013 | 8084 | 585 | 7560 | - | - |

```
                              SEQUENCE LISTING

<160> NUMBER OF SEQ ID NOS: 156

<210> SEQ ID NO 1
<211> LENGTH: 15
<212> TYPE: PRT
<213> ORGANISM: Mycobacterium tuberculosis

<400> SEQUENCE: 1

Ala Ala Ala Thr His Ser Pro Arg Asn Val Gln Phe Tyr Cys Ile
1               5                   10                  15

<210> SEQ ID NO 2
<211> LENGTH: 15
<212> TYPE: PRT
<213> ORGANISM: Mycobacterium tuberculosis

<400> SEQUENCE: 2

Ala Ala Ile Pro Leu Leu Thr Ala Pro Val Ile Gly Met Ala Met
1               5                   10                  15

<210> SEQ ID NO 3
<211> LENGTH: 15
<212> TYPE: PRT
<213> ORGANISM: Mycobacterium tuberculosis

<400> SEQUENCE: 3

Ala Ala Gln Val Trp Ser Gln Cys His Ser Tyr Gly Phe Asp Ala
1               5                   10                  15

<210> SEQ ID NO 4
<211> LENGTH: 15
<212> TYPE: PRT
<213> ORGANISM: Mycobacterium tuberculosis

<400> SEQUENCE: 4

Ala Asp Glu Glu Gln Gln Gln Ala Leu Ser Ser Gln Met Gly Phe
1               5                   10                  15

<210> SEQ ID NO 5
<211> LENGTH: 15
<212> TYPE: PRT
<213> ORGANISM: Mycobacterium tuberculosis

<400> SEQUENCE: 5

Ala Phe Glu Trp Tyr Tyr Gln Ser Gly Leu Ser Ile Val Met Pro
1               5                   10                  15

<210> SEQ ID NO 6
<211> LENGTH: 15
<212> TYPE: PRT
<213> ORGANISM: Mycobacterium tuberculosis

<400> SEQUENCE: 6

Ala Ile Gly Leu Gly Gly Gly Ala Gly Gly Asp Gly Gly Gln Gly
1               5                   10                  15

<210> SEQ ID NO 7
<211> LENGTH: 15
```

```
<212> TYPE: PRT
<213> ORGANISM: Mycobacterium tuberculosis

<400> SEQUENCE: 7

Ala Lys Leu Ile Ile Trp Tyr Pro His Tyr Ala Trp Leu Leu Leu
1               5                   10                  15

<210> SEQ ID NO 8
<211> LENGTH: 15
<212> TYPE: PRT
<213> ORGANISM: Mycobacterium tuberculosis

<400> SEQUENCE: 8

Ala Met Glu Asp Leu Val Arg Ala Tyr His Ala Met Ser Ser Thr
1               5                   10                  15

<210> SEQ ID NO 9
<211> LENGTH: 15
<212> TYPE: PRT
<213> ORGANISM: Mycobacterium tuberculosis

<400> SEQUENCE: 9

Ala Asn Asn Trp Tyr Gln Pro Ala Arg Arg Gly Phe Ser Thr Gly
1               5                   10                  15

<210> SEQ ID NO 10
<211> LENGTH: 15
<212> TYPE: PRT
<213> ORGANISM: Mycobacterium tuberculosis

<400> SEQUENCE: 10

Ala Pro Ala Pro Ile Ala Ser Pro Ile Pro Val Gly Ala Pro Gly
1               5                   10                  15

<210> SEQ ID NO 11
<211> LENGTH: 15
<212> TYPE: PRT
<213> ORGANISM: Mycobacterium tuberculosis

<400> SEQUENCE: 11

Ala Arg Glu Val Val Glu Leu Asp Arg Asp Glu Ala Met Arg Leu
1               5                   10                  15

<210> SEQ ID NO 12
<211> LENGTH: 15
<212> TYPE: PRT
<213> ORGANISM: Mycobacterium tuberculosis

<400> SEQUENCE: 12

Ala Ser Gln Ser Thr Thr Asn Pro Ile Phe Gly Met Pro Ser Pro
1               5                   10                  15

<210> SEQ ID NO 13
<211> LENGTH: 15
<212> TYPE: PRT
<213> ORGANISM: Mycobacterium tuberculosis

<400> SEQUENCE: 13

Ala Ser Val Ser Ile Asp Gly Ala Gln Gln Ala Ser Val Ala Leu
1               5                   10                  15

<210> SEQ ID NO 14
<211> LENGTH: 15
<212> TYPE: PRT
<213> ORGANISM: Mycobacterium tuberculosis
```

<400> SEQUENCE: 14

Asp Ala Glu Arg Phe Gly Ala Arg Leu Val Ala Ser Pro Gln His
1               5                   10                  15

<210> SEQ ID NO 15
<211> LENGTH: 15
<212> TYPE: PRT
<213> ORGANISM: Mycobacterium tuberculosis

<400> SEQUENCE: 15

Asp Ala Leu Ala Gly Lys Gly Ala Ser Ala Ile Val Leu Arg Gly
1               5                   10                  15

<210> SEQ ID NO 16
<211> LENGTH: 15
<212> TYPE: PRT
<213> ORGANISM: Mycobacterium tuberculosis

<400> SEQUENCE: 16

Asp Gly Ile Thr Leu Phe Asn Pro Ala Ala Val Pro Ile Arg Arg
1               5                   10                  15

<210> SEQ ID NO 17
<211> LENGTH: 15
<212> TYPE: PRT
<213> ORGANISM: Mycobacterium tuberculosis

<400> SEQUENCE: 17

Asp Gly Thr His Gln Thr Leu Gln Gly Ala Asp Leu Thr Val Ile
1               5                   10                  15

<210> SEQ ID NO 18
<211> LENGTH: 15
<212> TYPE: PRT
<213> ORGANISM: Mycobacterium tuberculosis

<400> SEQUENCE: 18

Asp Gln Asp Thr Ala Glu Leu His Arg Arg Ala Thr His Phe Arg
1               5                   10                  15

<210> SEQ ID NO 19
<211> LENGTH: 15
<212> TYPE: PRT
<213> ORGANISM: Mycobacterium tuberculosis

<400> SEQUENCE: 19

Asp Val Ser Val Ala Gln Gly Val Thr Asn Leu His Thr Ala Ile
1               5                   10                  15

<210> SEQ ID NO 20
<211> LENGTH: 15
<212> TYPE: PRT
<213> ORGANISM: Mycobacterium tuberculosis

<400> SEQUENCE: 20

Asp Tyr Ala Ile Val Gly Gly Ala Pro Gly Ser Ala Pro Arg Glu
1               5                   10                  15

<210> SEQ ID NO 21
<211> LENGTH: 15
<212> TYPE: PRT
<213> ORGANISM: Mycobacterium tuberculosis

<400> SEQUENCE: 21

Glu Ala Arg Arg Ala Asp Leu Gly Cys Asp Ile Val Asp Ala Thr
1               5                   10                  15

<210> SEQ ID NO 22
<211> LENGTH: 15
<212> TYPE: PRT
<213> ORGANISM: Mycobacterium tuberculosis

<400> SEQUENCE: 22

Glu Phe Pro Asp Leu Glu Gly Gln Val Gln Asp Leu Ala Ala Gln
1               5                   10                  15

<210> SEQ ID NO 23
<211> LENGTH: 15
<212> TYPE: PRT
<213> ORGANISM: Mycobacterium tuberculosis

<400> SEQUENCE: 23

Glu Gly Leu Trp Ala Gly Val Val Ile Pro Glu Ser Gly Arg Ala
1               5                   10                  15

<210> SEQ ID NO 24
<211> LENGTH: 15
<212> TYPE: PRT
<213> ORGANISM: Mycobacterium tuberculosis

<400> SEQUENCE: 24

Glu Ser Pro Ala Pro His Val Pro Ser His Gly Pro His Gln Pro
1               5                   10                  15

<210> SEQ ID NO 25
<211> LENGTH: 15
<212> TYPE: PRT
<213> ORGANISM: Mycobacterium tuberculosis

<400> SEQUENCE: 25

Phe Asp Glu Thr Ile Asp Lys Ser Thr Asp Lys Thr Leu His Ser
1               5                   10                  15

<210> SEQ ID NO 26
<211> LENGTH: 15
<212> TYPE: PRT
<213> ORGANISM: Mycobacterium tuberculosis

<400> SEQUENCE: 26

Phe Asp Trp Arg Tyr Pro Pro Ser Pro Pro Gln Pro Thr Gln
1               5                   10                  15

<210> SEQ ID NO 27
<211> LENGTH: 15
<212> TYPE: PRT
<213> ORGANISM: Mycobacterium tuberculosis

<400> SEQUENCE: 27

Phe Leu Ile Ile Asp Gly Trp Pro Gly Phe Val Gly Glu Phe Pro
1               5                   10                  15

<210> SEQ ID NO 28
<211> LENGTH: 15
<212> TYPE: PRT
<213> ORGANISM: Mycobacterium tuberculosis

<400> SEQUENCE: 28

Phe Pro Gln Tyr Arg Glu Leu Gly Val Tyr Leu Val Arg Gly Ile

```
1               5                   10                  15
```

<210> SEQ ID NO 29
<211> LENGTH: 15
<212> TYPE: PRT
<213> ORGANISM: Mycobacterium tuberculosis

<400> SEQUENCE: 29

```
Phe Gln Ile His Asp Pro Thr Thr Lys Asp Arg Gln Gly Asn Asp
1               5                   10                  15
```

<210> SEQ ID NO 30
<211> LENGTH: 15
<212> TYPE: PRT
<213> ORGANISM: Mycobacterium tuberculosis

<400> SEQUENCE: 30

```
Phe Ser Ile Val Arg Arg Ser Ser Arg Pro Glu Pro Ser Pro Arg
1               5                   10                  15
```

<210> SEQ ID NO 31
<211> LENGTH: 15
<212> TYPE: PRT
<213> ORGANISM: Mycobacterium tuberculosis

<400> SEQUENCE: 31

```
Gly Ala Gly Gly Ser Leu Thr Arg Thr Pro Leu Met Ser Gln Leu
1               5                   10                  15
```

<210> SEQ ID NO 32
<211> LENGTH: 15
<212> TYPE: PRT
<213> ORGANISM: Mycobacterium tuberculosis

<400> SEQUENCE: 32

```
Gly Ala Gly Ser Gly Phe Ala Asn Phe Gly Ser Leu Gly Ser Gly
1               5                   10                  15
```

<210> SEQ ID NO 33
<211> LENGTH: 15
<212> TYPE: PRT
<213> ORGANISM: Mycobacterium tuberculosis

<400> SEQUENCE: 33

```
Gly Cys Gly Thr Cys Asn Ile Ala Glu Ala Leu Lys Met Ser Leu
1               5                   10                  15
```

<210> SEQ ID NO 34
<211> LENGTH: 15
<212> TYPE: PRT
<213> ORGANISM: Mycobacterium tuberculosis

<400> SEQUENCE: 34

```
Gly Asp Phe Tyr Ala Gly Glu Lys Ser Met Thr Leu Asp Arg Ala
1               5                   10                  15
```

<210> SEQ ID NO 35
<211> LENGTH: 15
<212> TYPE: PRT
<213> ORGANISM: Mycobacterium tuberculosis

<400> SEQUENCE: 35

```
Gly Phe Asp Phe Thr Ala Gln Gly Val Trp Ala Phe Ala Arg Pro
1               5                   10                  15
```

```
<210> SEQ ID NO 36
<211> LENGTH: 15
<212> TYPE: PRT
<213> ORGANISM: Mycobacterium tuberculosis

<400> SEQUENCE: 36

Gly Gly Ala Pro Gln Thr Gly Lys Ser Thr Leu Leu Gln Thr Met
1               5                   10                  15

<210> SEQ ID NO 37
<211> LENGTH: 15
<212> TYPE: PRT
<213> ORGANISM: Mycobacterium tuberculosis

<400> SEQUENCE: 37

Gly Gly Ala Arg Phe Ala Val Glu Gln Gly His Gly Val Ala Leu
1               5                   10                  15

<210> SEQ ID NO 38
<211> LENGTH: 15
<212> TYPE: PRT
<213> ORGANISM: Mycobacterium tuberculosis

<400> SEQUENCE: 38

Gly Gly Arg Glu Gly Pro Thr Ala Gln Ile Ser Ala Gly Phe Cys
1               5                   10                  15

<210> SEQ ID NO 39
<211> LENGTH: 15
<212> TYPE: PRT
<213> ORGANISM: Mycobacterium tuberculosis

<400> SEQUENCE: 39

Gly Ile Ala Phe Gly Leu Phe Ile Val Thr Asn Ala Ala Lys Leu
1               5                   10                  15

<210> SEQ ID NO 40
<211> LENGTH: 15
<212> TYPE: PRT
<213> ORGANISM: Mycobacterium tuberculosis

<400> SEQUENCE: 40

Gly Leu Asp Pro Val Asn Tyr Gln Asn Phe Ala Val Thr Asn Asp
1               5                   10                  15

<210> SEQ ID NO 41
<211> LENGTH: 15
<212> TYPE: PRT
<213> ORGANISM: Mycobacterium tuberculosis

<400> SEQUENCE: 41

Gly Leu Tyr Asn Thr Gly Gly Leu Pro Pro Gly Thr Pro Ala Val
1               5                   10                  15

<210> SEQ ID NO 42
<211> LENGTH: 15
<212> TYPE: PRT
<213> ORGANISM: Mycobacterium tuberculosis

<400> SEQUENCE: 42

Gly Asn Ala Gly Leu Phe Gly Asp Gly Gly Ala Gly Gly Asp Gly
1               5                   10                  15

<210> SEQ ID NO 43
```

```
<211> LENGTH: 15
<212> TYPE: PRT
<213> ORGANISM: Mycobacterium tuberculosis

<400> SEQUENCE: 43

Gly Pro Ser Ile Gln Ala Arg Leu Arg Ala Glu Glu Ala Ser Gly
1               5                   10                  15

<210> SEQ ID NO 44
<211> LENGTH: 15
<212> TYPE: PRT
<213> ORGANISM: Mycobacterium tuberculosis

<400> SEQUENCE: 44

Gly Arg Gly Ala Pro Glu Asp Ala Pro Leu Ile Met Arg Gly Lys
1               5                   10                  15

<210> SEQ ID NO 45
<211> LENGTH: 15
<212> TYPE: PRT
<213> ORGANISM: Mycobacterium tuberculosis

<400> SEQUENCE: 45

Gly Thr Thr Gln Phe Gly Asp Thr Thr Ala Asn Lys Asp Ala Trp
1               5                   10                  15

<210> SEQ ID NO 46
<211> LENGTH: 15
<212> TYPE: PRT
<213> ORGANISM: Mycobacterium tuberculosis

<400> SEQUENCE: 46

His Leu Ala Lys Gly Glu Leu Arg Ser Ile His Asn Arg Thr Asp
1               5                   10                  15

<210> SEQ ID NO 47
<211> LENGTH: 15
<212> TYPE: PRT
<213> ORGANISM: Mycobacterium tuberculosis

<400> SEQUENCE: 47

His Leu Arg Glu Lys Gly Val Lys Leu Glu Ala Gln Arg Pro His
1               5                   10                  15

<210> SEQ ID NO 48
<211> LENGTH: 15
<212> TYPE: PRT
<213> ORGANISM: Mycobacterium tuberculosis

<400> SEQUENCE: 48

His Arg His Pro Ser Ala Asn Gln Gln Met Leu Trp Thr Leu Val
1               5                   10                  15

<210> SEQ ID NO 49
<211> LENGTH: 15
<212> TYPE: PRT
<213> ORGANISM: Mycobacterium tuberculosis

<400> SEQUENCE: 49

His Val Lys Pro Thr Gly Ser Ala Val Val Gly Leu Ser Met Ala
1               5                   10                  15

<210> SEQ ID NO 50
<211> LENGTH: 15
<212> TYPE: PRT
```

```
<213> ORGANISM: Mycobacterium tuberculosis

<400> SEQUENCE: 50

His Tyr Leu His Val Arg Pro Ala Asp Gln Phe Asp Ala Met Ile
1               5                   10                  15

<210> SEQ ID NO 51
<211> LENGTH: 15
<212> TYPE: PRT
<213> ORGANISM: Mycobacterium tuberculosis

<400> SEQUENCE: 51

Ile Glu Leu Thr Lys Arg Thr Leu Trp Ser Gly Leu Asp Ala Ala
1               5                   10                  15

<210> SEQ ID NO 52
<211> LENGTH: 15
<212> TYPE: PRT
<213> ORGANISM: Mycobacterium tuberculosis

<400> SEQUENCE: 52

Ile Leu Leu Glu Cys Thr Met Ala Gly Met Ala Thr Cys Thr Leu
1               5                   10                  15

<210> SEQ ID NO 53
<211> LENGTH: 15
<212> TYPE: PRT
<213> ORGANISM: Mycobacterium tuberculosis

<400> SEQUENCE: 53

Ile Pro Ile Gly Leu Arg Glu Thr Asp Leu Thr Pro Ala His Cys
1               5                   10                  15

<210> SEQ ID NO 54
<211> LENGTH: 15
<212> TYPE: PRT
<213> ORGANISM: Mycobacterium tuberculosis

<400> SEQUENCE: 54

Ile Thr Tyr Gln Ala Trp Gln Ala Gln Trp Asn Gln Ala Met Glu
1               5                   10                  15

<210> SEQ ID NO 55
<211> LENGTH: 15
<212> TYPE: PRT
<213> ORGANISM: Mycobacterium tuberculosis

<400> SEQUENCE: 55

Ile Val Gly Ala Ala Gly Gly Met Pro Pro Met Ala Pro Leu Ala
1               5                   10                  15

<210> SEQ ID NO 56
<211> LENGTH: 15
<212> TYPE: PRT
<213> ORGANISM: Mycobacterium tuberculosis

<400> SEQUENCE: 56

Lys Gly Arg Ser Ser Glu Met Ile Ile Cys Gly Gly Val Asn Ile
1               5                   10                  15

<210> SEQ ID NO 57
<211> LENGTH: 15
<212> TYPE: PRT
<213> ORGANISM: Mycobacterium tuberculosis
```

```
<400> SEQUENCE: 57

Lys Val Lys Pro Gln Lys Pro Lys Ala Thr Lys Pro Pro Lys Val
1               5                   10                  15

<210> SEQ ID NO 58
<211> LENGTH: 15
<212> TYPE: PRT
<213> ORGANISM: Mycobacterium tuberculosis

<400> SEQUENCE: 58

Lys Tyr Val Glu Ala Asp Leu Arg Val Leu Asp Glu Ile Ala Pro
1               5                   10                  15

<210> SEQ ID NO 59
<211> LENGTH: 15
<212> TYPE: PRT
<213> ORGANISM: Mycobacterium tuberculosis

<400> SEQUENCE: 59

Leu Ala Ala Pro Val Asp Pro Ser Thr Pro Ala Pro Ser Thr Thr
1               5                   10                  15

<210> SEQ ID NO 60
<211> LENGTH: 15
<212> TYPE: PRT
<213> ORGANISM: Mycobacterium tuberculosis

<400> SEQUENCE: 60

Leu Ala Ile Pro Gly Thr Asn Trp Ile Gly Gln Ala Ala Glu Ala
1               5                   10                  15

<210> SEQ ID NO 61
<211> LENGTH: 15
<212> TYPE: PRT
<213> ORGANISM: Mycobacterium tuberculosis

<400> SEQUENCE: 61

Leu Asp Trp Glu Arg Asn Phe Leu Arg Gln Leu Gln Ser His Arg
1               5                   10                  15

<210> SEQ ID NO 62
<211> LENGTH: 15
<212> TYPE: PRT
<213> ORGANISM: Mycobacterium tuberculosis

<400> SEQUENCE: 62

Leu Gly Gly Gly Val Ala Ala Asn Leu Gly Arg Ala Ala Ser Val
1               5                   10                  15

<210> SEQ ID NO 63
<211> LENGTH: 15
<212> TYPE: PRT
<213> ORGANISM: Mycobacterium tuberculosis

<400> SEQUENCE: 63

Leu Gly Asn Ser Val Tyr Thr Ser Asn Ala Gln Leu Val Val Tyr
1               5                   10                  15

<210> SEQ ID NO 64
<211> LENGTH: 15
<212> TYPE: PRT
<213> ORGANISM: Mycobacterium tuberculosis

<400> SEQUENCE: 64
```

Leu Gly Gln Pro Arg Ser Tyr Leu Ala Pro Pro Thr Arg Pro Ala
1               5                   10                  15

<210> SEQ ID NO 65
<211> LENGTH: 15
<212> TYPE: PRT
<213> ORGANISM: Mycobacterium tuberculosis

<400> SEQUENCE: 65

Leu Leu Ser Gln Gly Lys Phe Pro Tyr Lys Ser Ser Trp Ile Glu
1               5                   10                  15

<210> SEQ ID NO 66
<211> LENGTH: 15
<212> TYPE: PRT
<213> ORGANISM: Mycobacterium tuberculosis

<400> SEQUENCE: 66

Leu Asn Thr Ala Arg Leu Met Ala Gly Ala Gly Pro Ala Pro Met
1               5                   10                  15

<210> SEQ ID NO 67
<211> LENGTH: 15
<212> TYPE: PRT
<213> ORGANISM: Mycobacterium tuberculosis

<400> SEQUENCE: 67

Leu Pro Gly Thr Ala Val Ala Asn Pro Val Asp Pro Ala Arg Ile
1               5                   10                  15

<210> SEQ ID NO 68
<211> LENGTH: 15
<212> TYPE: PRT
<213> ORGANISM: Mycobacterium tuberculosis

<400> SEQUENCE: 68

Leu Gln Val Ile Glu Arg Thr Trp Arg Tyr Leu Lys Val Pro Cys
1               5                   10                  15

<210> SEQ ID NO 69
<211> LENGTH: 15
<212> TYPE: PRT
<213> ORGANISM: Mycobacterium tuberculosis

<400> SEQUENCE: 69

Leu Arg Cys Gly Asp Phe Ala Leu Gly Gly Pro Gln Gly Arg Gly
1               5                   10                  15

<210> SEQ ID NO 70
<211> LENGTH: 15
<212> TYPE: PRT
<213> ORGANISM: Mycobacterium tuberculosis

<400> SEQUENCE: 70

Leu Arg Ile Leu Lys Thr Asp Ile Tyr Ala Pro Thr Gly Ala Val
1               5                   10                  15

<210> SEQ ID NO 71
<211> LENGTH: 15
<212> TYPE: PRT
<213> ORGANISM: Mycobacterium tuberculosis

<400> SEQUENCE: 71

Leu Thr Tyr Trp Thr Ala Gly Asp Thr Arg Asn Arg Gly Arg Glu
1               5                   10                  15

<210> SEQ ID NO 72
<211> LENGTH: 15
<212> TYPE: PRT
<213> ORGANISM: Mycobacterium tuberculosis

<400> SEQUENCE: 72

Met Ala Gly Asp Thr Thr Ile Thr Ile Val Gly Asn Leu Thr Ala
1               5                   10                  15

<210> SEQ ID NO 73
<211> LENGTH: 15
<212> TYPE: PRT
<213> ORGANISM: Mycobacterium tuberculosis

<400> SEQUENCE: 73

Met Ala Ser Gly Ser Gly Leu Cys Lys Thr Thr Ser Asn Phe Ile
1               5                   10                  15

<210> SEQ ID NO 74
<211> LENGTH: 15
<212> TYPE: PRT
<213> ORGANISM: Mycobacterium tuberculosis

<400> SEQUENCE: 74

Met Glu Leu Leu Asp Ala Phe Gly Ile Ala Met Ala Gly Ala Pro
1               5                   10                  15

<210> SEQ ID NO 75
<211> LENGTH: 15
<212> TYPE: PRT
<213> ORGANISM: Mycobacterium tuberculosis

<400> SEQUENCE: 75

Met Gly Thr Thr Leu Thr Ala Ile Leu Phe Ala Gly Asn Arg Leu
1               5                   10                  15

<210> SEQ ID NO 76
<211> LENGTH: 15
<212> TYPE: PRT
<213> ORGANISM: Mycobacterium tuberculosis

<400> SEQUENCE: 76

Met Ile Asp Gly Val Tyr Lys Val Cys Lys Gly Leu Glu Lys Ile
1               5                   10                  15

<210> SEQ ID NO 77
<211> LENGTH: 15
<212> TYPE: PRT
<213> ORGANISM: Mycobacterium tuberculosis

<400> SEQUENCE: 77

Met Lys Leu Thr Thr Met Ile Lys Thr Ala Val Ala Val Val Ala
1               5                   10                  15

<210> SEQ ID NO 78
<211> LENGTH: 15
<212> TYPE: PRT
<213> ORGANISM: Mycobacterium tuberculosis

<400> SEQUENCE: 78

Met Asn Ser Ala Ile Ile Lys Ile Ala Lys Trp Ala Gln Ser Gln
1               5                   10                  15

```
<210> SEQ ID NO 79
<211> LENGTH: 15
<212> TYPE: PRT
<213> ORGANISM: Mycobacterium tuberculosis

<400> SEQUENCE: 79

Met Gln Leu Val Asp Arg Val Arg Gly Ala Val Thr Gly Met Ser
1               5                   10                  15

<210> SEQ ID NO 80
<211> LENGTH: 15
<212> TYPE: PRT
<213> ORGANISM: Mycobacterium tuberculosis

<400> SEQUENCE: 80

Met Arg Leu Ser Leu Thr Ala Leu Ser Ala Gly Val Gly Ala Val
1               5                   10                  15

<210> SEQ ID NO 81
<211> LENGTH: 15
<212> TYPE: PRT
<213> ORGANISM: Mycobacterium tuberculosis

<400> SEQUENCE: 81

Met Ser Ala Pro Ala Val Ala Ala Gly Pro Thr Ala Ala Gly Ala
1               5                   10                  15

<210> SEQ ID NO 82
<211> LENGTH: 15
<212> TYPE: PRT
<213> ORGANISM: Mycobacterium tuberculosis

<400> SEQUENCE: 82

Asn Ala Glu Ile Ala Ala Thr Ile Ala Asn Gly Gly Ile Thr Met
1               5                   10                  15

<210> SEQ ID NO 83
<211> LENGTH: 15
<212> TYPE: PRT
<213> ORGANISM: Mycobacterium tuberculosis

<400> SEQUENCE: 83

Asn Ala Arg Thr Ala Asp Gly Ile Asn Tyr Arg Val Leu Trp Gln
1               5                   10                  15

<210> SEQ ID NO 84
<211> LENGTH: 15
<212> TYPE: PRT
<213> ORGANISM: Mycobacterium tuberculosis

<400> SEQUENCE: 84

Asn Asp Pro Asp Arg Ala Ser Met Leu Phe Glu Gly Ser Thr Ile
1               5                   10                  15

<210> SEQ ID NO 85
<211> LENGTH: 15
<212> TYPE: PRT
<213> ORGANISM: Mycobacterium tuberculosis

<400> SEQUENCE: 85

Asn Lys Pro Val Ile Ser Trp Ala Gly Asp Asn Gly Ile Tyr Phe
1               5                   10                  15

<210> SEQ ID NO 86
<211> LENGTH: 15
```

-continued

<212> TYPE: PRT
<213> ORGANISM: Mycobacterium tuberculosis

<400> SEQUENCE: 86

Asn Val Asp Gly Ala Gln Arg Glu Ile Asp Ile Leu Glu Asn Asp
1               5                   10                  15

<210> SEQ ID NO 87
<211> LENGTH: 15
<212> TYPE: PRT
<213> ORGANISM: Mycobacterium tuberculosis

<400> SEQUENCE: 87

Asn Val Asp Gly Ala Gln Arg Glu Ile Asp Ile Leu Glu Asn Asp
1               5                   10                  15

<210> SEQ ID NO 88
<211> LENGTH: 15
<212> TYPE: PRT
<213> ORGANISM: Mycobacterium tuberculosis

<400> SEQUENCE: 88

Pro Ala Asn Arg Pro Gly Arg Ala Val Ser Met Glu Lys His His
1               5                   10                  15

<210> SEQ ID NO 89
<211> LENGTH: 15
<212> TYPE: PRT
<213> ORGANISM: Mycobacterium tuberculosis

<400> SEQUENCE: 89

Pro Leu Asp Asp Gly Asp Val Ile Asp Ser Met Phe Met Ser Lys
1               5                   10                  15

<210> SEQ ID NO 90
<211> LENGTH: 15
<212> TYPE: PRT
<213> ORGANISM: Mycobacterium tuberculosis

<400> SEQUENCE: 90

Pro Leu Gln Ala Leu Gln Thr Val Gln Gln Asn Val Leu Thr Val
1               5                   10                  15

<210> SEQ ID NO 91
<211> LENGTH: 15
<212> TYPE: PRT
<213> ORGANISM: Mycobacterium tuberculosis

<400> SEQUENCE: 91

Pro Pro Ala Ala Thr Gln Thr Leu Gly Gln Leu Gly Glu Met Ser
1               5                   10                  15

<210> SEQ ID NO 92
<211> LENGTH: 15
<212> TYPE: PRT
<213> ORGANISM: Mycobacterium tuberculosis

<400> SEQUENCE: 92

Pro Pro Gly Asp Glu Arg His Met Leu Trp Phe Glu Leu Met Lys
1               5                   10                  15

<210> SEQ ID NO 93
<211> LENGTH: 15
<212> TYPE: PRT
<213> ORGANISM: Mycobacterium tuberculosis

<400> SEQUENCE: 93

Pro Pro Ile Arg Ala Pro Gly Gly Asp Ala Ala Asp Thr Arg Leu
1               5                   10                  15

<210> SEQ ID NO 94
<211> LENGTH: 15
<212> TYPE: PRT
<213> ORGANISM: Mycobacterium tuberculosis

<400> SEQUENCE: 94

Pro Pro Thr Pro Pro Met Pro Ile Ala Gly Pro Glu Pro Ala Pro
1               5                   10                  15

<210> SEQ ID NO 95
<211> LENGTH: 15
<212> TYPE: PRT
<213> ORGANISM: Mycobacterium tuberculosis

<400> SEQUENCE: 95

Pro Ser Gly Gly Pro Val Ala Ala Ser Ala Ala Pro Ser Ile Pro
1               5                   10                  15

<210> SEQ ID NO 96
<211> LENGTH: 15
<212> TYPE: PRT
<213> ORGANISM: Mycobacterium tuberculosis

<400> SEQUENCE: 96

Pro Ser Gly Thr Ala Val Gly Ala Gly Ala Arg Ser Ser Val Gly
1               5                   10                  15

<210> SEQ ID NO 97
<211> LENGTH: 15
<212> TYPE: PRT
<213> ORGANISM: Mycobacterium tuberculosis

<400> SEQUENCE: 97

Gln Ala Gln Leu Ile Ser Ser Gln Ala Gln Gln Gly Gly Gln Gln
1               5                   10                  15

<210> SEQ ID NO 98
<211> LENGTH: 15
<212> TYPE: PRT
<213> ORGANISM: Mycobacterium tuberculosis

<400> SEQUENCE: 98

Gln Glu Ala Gly Asn Phe Glu Arg Ile Ser Gly Asp Leu Lys Thr
1               5                   10                  15

<210> SEQ ID NO 99
<211> LENGTH: 15
<212> TYPE: PRT
<213> ORGANISM: Mycobacterium tuberculosis

<400> SEQUENCE: 99

Gln Met Gln Asp Ala Phe Glu Thr Gly Val Met Phe Ser Leu His
1               5                   10                  15

<210> SEQ ID NO 100
<211> LENGTH: 15
<212> TYPE: PRT
<213> ORGANISM: Mycobacterium tuberculosis

<400> SEQUENCE: 100

Gln Ser Gly Pro Ala His Ala Asp Glu Ser Ala Ala Ser Val Thr
1               5                   10                  15

<210> SEQ ID NO 101
<211> LENGTH: 15
<212> TYPE: PRT
<213> ORGANISM: Mycobacterium tuberculosis

<400> SEQUENCE: 101

Arg Gly Ile Pro Pro Gly His Val Gly Val Ala Trp Arg Gly Thr
1               5                   10                  15

<210> SEQ ID NO 102
<211> LENGTH: 15
<212> TYPE: PRT
<213> ORGANISM: Mycobacterium tuberculosis

<400> SEQUENCE: 102

Arg Asn Ile Ile Asp Met His Leu Pro Arg His Arg Leu Asp Ser
1               5                   10                  15

<210> SEQ ID NO 103
<211> LENGTH: 15
<212> TYPE: PRT
<213> ORGANISM: Mycobacterium tuberculosis

<400> SEQUENCE: 103

Arg Gln Arg Arg Thr Lys Gly Ala Gly Gly Ser Phe Thr Ser Arg
1               5                   10                  15

<210> SEQ ID NO 104
<211> LENGTH: 15
<212> TYPE: PRT
<213> ORGANISM: Mycobacterium tuberculosis

<400> SEQUENCE: 104

Arg Arg His Leu Gln Asp Val Trp Gly Val Asp Val Ser Gly Ala
1               5                   10                  15

<210> SEQ ID NO 105
<211> LENGTH: 15
<212> TYPE: PRT
<213> ORGANISM: Mycobacterium tuberculosis

<400> SEQUENCE: 105

Arg Ser Glu Pro Asp Lys Val Asn Arg Val Val Ala Glu Met Gln
1               5                   10                  15

<210> SEQ ID NO 106
<211> LENGTH: 15
<212> TYPE: PRT
<213> ORGANISM: Mycobacterium tuberculosis

<400> SEQUENCE: 106

Arg Thr Tyr Ser Gln Ile Asp Asp Gly Ala Ala Gly Val Phe Ala
1               5                   10                  15

<210> SEQ ID NO 107
<211> LENGTH: 15
<212> TYPE: PRT
<213> ORGANISM: Mycobacterium tuberculosis

<400> SEQUENCE: 107

Ser Ala Ala Ser Val Thr Pro Ala Ala Ala Ser Gly Val Pro Gly

```
1               5                   10                  15
```

<210> SEQ ID NO 108
<211> LENGTH: 15
<212> TYPE: PRT
<213> ORGANISM: Mycobacterium tuberculosis

<400> SEQUENCE: 108

```
Ser Ala Asp Asp Gly Thr Pro Val Ser Met Ile Pro Val Ser Ala
1               5                   10                  15
```

<210> SEQ ID NO 109
<211> LENGTH: 15
<212> TYPE: PRT
<213> ORGANISM: Mycobacterium tuberculosis

<400> SEQUENCE: 109

```
Ser Ala Lys Met Leu Ser Val Val Pro Leu Met Ala Gly Gly Gly
1               5                   10                  15
```

<210> SEQ ID NO 110
<211> LENGTH: 15
<212> TYPE: PRT
<213> ORGANISM: Mycobacterium tuberculosis

<400> SEQUENCE: 110

```
Ser Asp Val Phe Thr Thr Ile Thr Pro Ala Thr Ala Gln Gly Ile
1               5                   10                  15
```

<210> SEQ ID NO 111
<211> LENGTH: 15
<212> TYPE: PRT
<213> ORGANISM: Mycobacterium tuberculosis

<400> SEQUENCE: 111

```
Ser Lys Ala Ala Thr Asp Met Leu Ala Tyr Gln Tyr His Lys Ser
1               5                   10                  15
```

<210> SEQ ID NO 112
<211> LENGTH: 15
<212> TYPE: PRT
<213> ORGANISM: Mycobacterium tuberculosis

<400> SEQUENCE: 112

```
Ser Lys Ile Pro Arg Gly Glu Glu Ala Gly Lys Leu Trp Asp Ala
1               5                   10                  15
```

<210> SEQ ID NO 113
<211> LENGTH: 15
<212> TYPE: PRT
<213> ORGANISM: Mycobacterium tuberculosis

<400> SEQUENCE: 113

```
Ser Lys Leu Met Thr Arg Ile Ala Gly Ala Gly Ala Met Gly Ser
1               5                   10                  15
```

<210> SEQ ID NO 114
<211> LENGTH: 15
<212> TYPE: PRT
<213> ORGANISM: Mycobacterium tuberculosis

<400> SEQUENCE: 114

```
Ser Leu Phe Pro Glu Phe Ser Glu Leu Phe Ala Ala Phe Pro Ser
1               5                   10                  15
```

<210> SEQ ID NO 115
<211> LENGTH: 15
<212> TYPE: PRT
<213> ORGANISM: Mycobacterium tuberculosis

<400> SEQUENCE: 115

Ser Met Glu Lys His His Leu Met Ile Gly Val Pro Arg Phe Asp
1 5 10 15

<210> SEQ ID NO 116
<211> LENGTH: 15
<212> TYPE: PRT
<213> ORGANISM: Mycobacterium tuberculosis

<400> SEQUENCE: 116

Ser Pro Gly Gln Gln Pro Gly Gly Gly Val Pro Ala Gln Ala Met
1 5 10 15

<210> SEQ ID NO 117
<211> LENGTH: 15
<212> TYPE: PRT
<213> ORGANISM: Mycobacterium tuberculosis

<400> SEQUENCE: 117

Ser Gln Arg Gly Trp Arg His Trp Val His Ala Leu Thr Arg Ile
1 5 10 15

<210> SEQ ID NO 118
<211> LENGTH: 15
<212> TYPE: PRT
<213> ORGANISM: Mycobacterium tuberculosis

<400> SEQUENCE: 118

Ser Ser Thr His Glu Ala Asn Thr Met Ala Met Met Ala Arg Asp
1 5 10 15

<210> SEQ ID NO 119
<211> LENGTH: 15
<212> TYPE: PRT
<213> ORGANISM: Mycobacterium tuberculosis

<400> SEQUENCE: 119

Ser Thr Val Ser Gly Val Val Val Val Ala Ser Val Ser Ile Asp
1 5 10 15

<210> SEQ ID NO 120
<211> LENGTH: 15
<212> TYPE: PRT
<213> ORGANISM: Mycobacterium tuberculosis

<400> SEQUENCE: 120

Thr Ala Ser Asp Phe Trp Gly Gly Ala Gly Ser Ala Ala Cys Gln
1 5 10 15

<210> SEQ ID NO 121
<211> LENGTH: 15
<212> TYPE: PRT
<213> ORGANISM: Mycobacterium tuberculosis

<400> SEQUENCE: 121

Thr Asp Ala Lys Leu Leu Ser Ser Ile Leu Thr Tyr His Val Ile
1 5 10 15

<210> SEQ ID NO 122

```
<211> LENGTH: 15
<212> TYPE: PRT
<213> ORGANISM: Mycobacterium tuberculosis

<400> SEQUENCE: 122

Thr Gly Gln Gly Asn Ser Leu Lys Val Gly Asn Ala Asp Val Val
1               5                   10                  15

<210> SEQ ID NO 123
<211> LENGTH: 15
<212> TYPE: PRT
<213> ORGANISM: Mycobacterium tuberculosis

<400> SEQUENCE: 123

Thr Leu Leu Gln Thr Met Val Met Ser Ala Ala Ala Thr His Ser
1               5                   10                  15

<210> SEQ ID NO 124
<211> LENGTH: 15
<212> TYPE: PRT
<213> ORGANISM: Mycobacterium tuberculosis

<400> SEQUENCE: 124

Thr Met Leu Val Val Pro Val Gly Ala Gly Pro Gly Leu Arg Glu
1               5                   10                  15

<210> SEQ ID NO 125
<211> LENGTH: 15
<212> TYPE: PRT
<213> ORGANISM: Mycobacterium tuberculosis

<400> SEQUENCE: 125

Thr Asn Ala Ala Lys Leu Thr Val Ala Val Ala Arg Ile Ala Leu
1               5                   10                  15

<210> SEQ ID NO 126
<211> LENGTH: 15
<212> TYPE: PRT
<213> ORGANISM: Mycobacterium tuberculosis

<400> SEQUENCE: 126

Thr Pro Lys Thr Lys Ile Glu Thr Ala Leu Asp Arg Gln Lys Ile
1               5                   10                  15

<210> SEQ ID NO 127
<211> LENGTH: 15
<212> TYPE: PRT
<213> ORGANISM: Mycobacterium tuberculosis

<400> SEQUENCE: 127

Thr Gln Ala Val Leu Thr Ala Thr Asn Phe Phe Gly Ile Asn Thr
1               5                   10                  15

<210> SEQ ID NO 128
<211> LENGTH: 15
<212> TYPE: PRT
<213> ORGANISM: Mycobacterium tuberculosis

<400> SEQUENCE: 128

Thr Arg Asp Lys Phe Leu Ser Ala Ala Thr Ser Ser Thr Pro Arg
1               5                   10                  15

<210> SEQ ID NO 129
<211> LENGTH: 15
<212> TYPE: PRT
```

<213> ORGANISM: Mycobacterium tuberculosis

<400> SEQUENCE: 129

Thr Arg Leu Met Arg Leu Glu Asp Glu Met Lys Glu Gly Arg Tyr
1               5                   10                  15

<210> SEQ ID NO 130
<211> LENGTH: 15
<212> TYPE: PRT
<213> ORGANISM: Mycobacterium tuberculosis

<400> SEQUENCE: 130

Thr Arg Gln Leu His Gln Leu Gly Leu Glu Ser Ser Glu Arg Glu
1               5                   10                  15

<210> SEQ ID NO 131
<211> LENGTH: 15
<212> TYPE: PRT
<213> ORGANISM: Mycobacterium tuberculosis

<400> SEQUENCE: 131

Thr Thr Gly Pro Lys Pro Leu Val Gln Asp Glu Tyr Ala Lys His
1               5                   10                  15

<210> SEQ ID NO 132
<211> LENGTH: 15
<212> TYPE: PRT
<213> ORGANISM: Mycobacterium tuberculosis

<400> SEQUENCE: 132

Thr Tyr Ser Gln Ile Asp Asp Gly Ala Ala Gly Val Phe Ala Glu
1               5                   10                  15

<210> SEQ ID NO 133
<211> LENGTH: 15
<212> TYPE: PRT
<213> ORGANISM: Mycobacterium tuberculosis

<400> SEQUENCE: 133

Val His Leu Ala Arg Asp Leu Arg Leu His Arg Asp Val Ala Val
1               5                   10                  15

<210> SEQ ID NO 134
<211> LENGTH: 15
<212> TYPE: PRT
<213> ORGANISM: Mycobacterium tuberculosis

<400> SEQUENCE: 134

Val Leu Asp Glu Ser Pro Glu Phe Asp Arg Thr Ala Leu Asn Arg
1               5                   10                  15

<210> SEQ ID NO 135
<211> LENGTH: 15
<212> TYPE: PRT
<213> ORGANISM: Mycobacterium tuberculosis

<400> SEQUENCE: 135

Val Leu Glu Ser Lys Thr Val Gly Asp Ser Cys Val Val Leu Glu
1               5                   10                  15

<210> SEQ ID NO 136
<211> LENGTH: 15
<212> TYPE: PRT
<213> ORGANISM: Mycobacterium tuberculosis

```
<400> SEQUENCE: 136

Val Thr Ser Leu Phe Ser Gln Val Gly Gly Thr Gly Gly Gly Asn
1               5                   10                  15

<210> SEQ ID NO 137
<211> LENGTH: 15
<212> TYPE: PRT
<213> ORGANISM: Mycobacterium tuberculosis

<400> SEQUENCE: 137

Val Val Val Gly Gly Ser Ile Asp Ala Ala Ile Asp Thr Ala Lys
1               5                   10                  15

<210> SEQ ID NO 138
<211> LENGTH: 15
<212> TYPE: PRT
<213> ORGANISM: Mycobacterium tuberculosis

<400> SEQUENCE: 138

Ala Pro His Glu Ser Phe Asp Thr Gln Tyr Thr Arg His Val Glu
1               5                   10                  15

<210> SEQ ID NO 139
<211> LENGTH: 15
<212> TYPE: PRT
<213> ORGANISM: Mycobacterium tuberculosis

<400> SEQUENCE: 139

Glu Ala Glu His Gln Ala Ile Ile Ser Asp Val Leu Thr Ala Ser
1               5                   10                  15

<210> SEQ ID NO 140
<211> LENGTH: 15
<212> TYPE: PRT
<213> ORGANISM: Mycobacterium tuberculosis

<400> SEQUENCE: 140

His Ala Arg Asp Val Leu Ala Asp Arg Arg Leu Phe Val Leu Thr
1               5                   10                  15

<210> SEQ ID NO 141
<211> LENGTH: 27
<212> TYPE: PRT
<213> ORGANISM: Mycobacterium tuberculosis

<400> SEQUENCE: 141

Ile His Ser Leu Leu Asp Glu Gly Lys Gln Ser Leu Thr Lys Leu Ala
1               5                   10                  15

Ala Ala Trp Gly Gly Ser Gly Ser Glu Ala Tyr
            20                  25

<210> SEQ ID NO 142
<211> LENGTH: 15
<212> TYPE: PRT
<213> ORGANISM: Mycobacterium tuberculosis

<400> SEQUENCE: 142

Lys Glu Leu His Leu Arg Leu Gly Thr Ala Thr Ala Asp Leu Ser
1               5                   10                  15

<210> SEQ ID NO 143
<211> LENGTH: 15
<212> TYPE: PRT
<213> ORGANISM: Mycobacterium tuberculosis
```

-continued

<400> SEQUENCE: 143

Lys Phe Arg Gln Leu Gly Asp Ile Val Leu Glu Leu Ala Ala Ala
1 5 10 15

<210> SEQ ID NO 144
<211> LENGTH: 15
<212> TYPE: PRT
<213> ORGANISM: Mycobacterium tuberculosis

<400> SEQUENCE: 144

Asn Ser Leu Val Thr Ala Thr His Gly Ala Asn Val Ser Leu Val
1 5 10 15

<210> SEQ ID NO 145
<211> LENGTH: 27
<212> TYPE: PRT
<213> ORGANISM: Mycobacterium tuberculosis

<400> SEQUENCE: 145

Thr Lys Leu Ala Ala Ala Trp Gly Gly Ser Gly Ser Glu Ala Tyr Gln
1 5 10 15

Gly Val Gln Gln Lys Trp Asp Ala Thr Ala Thr
20 25

<210> SEQ ID NO 146
<211> LENGTH: 15
<212> TYPE: PRT
<213> ORGANISM: Mycobacterium tuberculosis

<400> SEQUENCE: 146

Val Trp Arg Arg Asp Leu Arg Ala Ile Val Arg Leu Leu Ala Trp
1 5 10 15

<210> SEQ ID NO 147
<211> LENGTH: 15
<212> TYPE: PRT
<213> ORGANISM: Mycobacterium tuberculosis

<400> SEQUENCE: 147

Ala Pro Arg Ala Asp Leu Ala Thr Arg Glu Glu Gln Ile Ala Val
1 5 10 15

<210> SEQ ID NO 148
<211> LENGTH: 15
<212> TYPE: PRT
<213> ORGANISM: Mycobacterium tuberculosis

<400> SEQUENCE: 148

His Asp Ile Gln Val Thr Leu Ser Ala Gly Gln Ser Val Thr Leu
1 5 10 15

<210> SEQ ID NO 149
<211> LENGTH: 15
<212> TYPE: PRT
<213> ORGANISM: Mycobacterium tuberculosis

<400> SEQUENCE: 149

Ile Arg Thr Asn Gln Val Ser Thr Ile Leu Ala Ser Asp Gly Ser
1 5 10 15

<210> SEQ ID NO 150
<211> LENGTH: 15
<212> TYPE: PRT

<213> ORGANISM: Mycobacterium tuberculosis

<400> SEQUENCE: 150

Met Thr Glu Gln Gln Trp Asn Phe Ala Gly Ile Glu Ala Ala Ala
1               5                   10                  15

<210> SEQ ID NO 151
<211> LENGTH: 15
<212> TYPE: PRT
<213> ORGANISM: Mycobacterium tuberculosis

<400> SEQUENCE: 151

Ala Ala Ala Ser Ala Ile Gln Gly Asn Val Thr Ser Ile His Ser
1               5                   10                  15

<210> SEQ ID NO 152
<211> LENGTH: 15
<212> TYPE: PRT
<213> ORGANISM: Mycobacterium tuberculosis

<400> SEQUENCE: 152

Ile His Ser Leu Leu Asp Glu Gly Lys Gln Ser Leu Thr Lys Leu
1               5                   10                  15

<210> SEQ ID NO 153
<211> LENGTH: 15
<212> TYPE: PRT
<213> ORGANISM: Mycobacterium tuberculosis

<400> SEQUENCE: 153

Thr Lys Leu Ala Ala Ala Trp Gly Gly Ser Gly Ser Glu Ala Tyr
1               5                   10                  15

<210> SEQ ID NO 154
<211> LENGTH: 15
<212> TYPE: PRT
<213> ORGANISM: Mycobacterium tuberculosis

<400> SEQUENCE: 154

Glu Ala Tyr Gln Gly Val Gln Gln Lys Trp Asp Ala Thr Ala Thr
1               5                   10                  15

<210> SEQ ID NO 155
<211> LENGTH: 15
<212> TYPE: PRT
<213> ORGANISM: Mycobacterium tuberculosis

<400> SEQUENCE: 155

Glu Leu Asn Asn Ala Leu Gln Asn Leu Ala Arg Thr Ile Ser Glu
1               5                   10                  15

<210> SEQ ID NO 156
<211> LENGTH: 15
<212> TYPE: PRT
<213> ORGANISM: Mycobacterium tuberculosis

<400> SEQUENCE: 156

Gln Ala Met Ala Ser Thr Glu Gly Asn Val Thr Gly Met Phe Ala
1               5                   10                  15

MYCOBACTERIUM TUBERCULOSIS SPECIFIC PEPTIDES FOR DETECTION OF INFECTION OR IMMUNIZATION IN NON-HUMAN PRIMATES

CROSS-REFERENCE TO RELATED APPLICATIONS

This application is a continuation of U.S. patent application Ser. No. 15/212,478, filed Jul. 18, 2016, now U.S. Pat. No. 10,094,830, which is a continuation of U.S. patent application Ser. No. 14/373,286, filed Jul. 18, 2014, now U.S. Pat. No. 9,404,923, which is a national stage of International (PCT) Patent Application Serial No. PCT/US2013/025072, filed Feb. 7, 2013, which claims the benefit of and priority to U.S. Provisional Patent Application No. 61/595,805, filed Feb. 7, 2012, and to U.S. Provisional Patent Application No. 61/723,094, filed Nov. 6, 2012, the contents of each of which are hereby incorporated by reference for all purposes.

FIELD OF THE INVENTION

The present invention relates to novel peptides that may be used in whole or in combination for the detection of *Mycobacterium tuberculosis* infection. In particular, the present invention relates to compositions and methods involving detection of antibodies contained in the blood of non-human primates that arise from an infection from *M. tuberculosis* or vaccination using an epitope specific inoculation.

BACKGROUND OF THE INVENTION

The intracellular *bacillus* pathogen *Mycobacterium tuberculosis* (*M. tb*) causes the fatal and rapidly spreading disease tuberculosis (TB) in non-human primates (NHP), similar to active TB in humans. In NHPs, *M. tb* is typically spread by inhalation of aerosolized infectious particles expelled by infected individuals (humans and animals) [1]. Because of the health threat to captive primates and the zoonotic potential to and from their human caretakers, strict screening protocols have been implemented to prevent outbreaks[2]. Despite the precautions taken to prevent *M. tb* exposure in captive primate colonies, outbreaks continue to cause a major impact on colony health. Outbreaks result in animal losses, disruption of research, potential exposure to human caretakers, and the immeasurable costs to contain the outbreaks [3-11].

Current methods for TB screening in non-human primates rely on the bi-annual intradermal tuberculin skin test (TST), a test that has been routinely used for decades [2, 12]. Injection of *M. tb* antigen is typically performed in the eyelid, and relies on immune cell mediated recognition of the antigens generated by previous exposure to *M. tb*. The antigens currently used in the TST are semi-purified heterogeneous crude protein preparations of either mammalian old tuberculin (MOT) or purified protein derivative (PPD). The cell mediated response resulting in local inflammation and necrotic tissue measured by a TST takes at least 4 weeks after infection to develop and has some severe limitations in terms of diagnostic sensitivity and specificity. Additionally, the TST is labor intensive, and requires increased animal handling over the three days it takes to develop the response of a swelled eyelid or necrotic tissue.

While false positive TST results in loss of individually valuable research animals, the greatest threat to NHP colony and human health are false negative results, which make entire colonies vulnerable to outbreaks [5, 10, 13]. Because NHPs can develop latent TB without obvious clinical symptoms [3, 7, 14-15], false negative results or anergy to TST pose a significant threat to colony health when combined with the low diagnostic sensitivity of the TST. Anergy can also be induced in research primates by immunosuppressive treatment or disease, or concurrent viral infection like measles [4, 9, 16-17]. Additionally, reports of anergy to TST following measles vaccination complicates using the TST as part of importation quarantine procedure[18]. Despite the TST being USDA-approved for diagnostic testing of NHPs for TB, it is widely considered that a negative TST result does not reliably exclude tuberculosis infection (reports between 79 and 90% predictive value)[19]. It is, however, the standard for antemortem diagnostic testing and requires lengthy postmortem confirmation by the "gold standard" of mycobacterial culture and isolation.

Other immune-based screening assays and serological tests, including interferon gamma release assays (IGRA) and commercial antibody detection assays can have a higher sensitivity than the TST for acute infection, but rely on similar sets of *M. tb* recombinant proteins that often fail to identify latently infected animals. In the case of the commercially available IGRA test PRIMAGAM (Prionics AG, Zurich, Switzerland), the semi-purified PPD antigen set is used to stimulate IFN-γ release by whole blood leukocytes [19]. The PrimaTB STAT-PAK assay is a lateral flow device for measuring presence of TB-specific antibodies in NHP plasma or serum, and uses an antigen cocktail of recombinant antigens including ESAT-6, CFP-10, MPB83, and TBF10 (a fusion protein from Corixa Corp)[20]. Relative to the TST these tests are expensive, technically difficult, and impractical to perform on a colony-wide basis[19]. Moreover, these methods all rely on semi-purified or recombinant antigens for identifying a biological or antibody response, all are subject to the same limitations of sensitivity. At best, reported predictive value in experimentally infected animals is between 83 and 94% for PRIMAGAM and 80 and 94% for PrimaTB STAT-PAK, respectively [19-21]. Unpublished studies have reported significantly lower predictive value (<50%) for naturally occurring infections in NHPs (Table 2). Current recommendations for TB testing include routine TST in conjunction with IGRA or antibody assays for routine screening because no one test is both sensitive and specific enough[22].

What is needed in the art are improved devices and methods for determining if a subject animal has tuberculosis, and especially devices and methods which allow for accurate, specific and sensitive monitoring of primate colonies.

SUMMARY OF THE INVENTION

The present invention relates to novel peptides that may be used in whole or in combination for the detection of *Mycobacterium tuberculosis* infection. In particular, the present invention relates to compositions and methods involving detection of antibodies contained in the blood of non-human primates that arise from an infection from *M. tuberculosis* or vaccination using an epitope specific inoculation. More particularly, the present invention provides a means to distinguish early, active, and latent *M. tuberculosis* infection. More particularly, the present invention describes an immunological diagnostic mechanism for the detection of *M. tuberculosis* infection.

Accordingly, in some embodiments, the present invention provides an immunoassay device comprising one or more capture reagents comprising a peptide selected from the group consisting of SEQ ID NOs.1-149. In some embodiments, the device comprises two or more capture reagents, each comprising a different peptide selected from the group consisting of SEQ ID NOs.1-149. In some embodiments, the device comprises three or more capture reagents, each comprising a different peptide selected from the group consisting of SEQ ID NOs.1-149. In some embodiments, the device comprises four or more capture reagents, each comprising a different peptide selected from the group consisting of SEQ ID NOs.1-149. In some embodiments, the device comprises five or more capture reagents, each comprising a different peptide selected from the group consisting of SEQ ID NOs.1-149. In some embodiments, the device comprises ten or more capture reagents, each comprising a different peptide selected from the group consisting of SEQ ID NOs.1-149. In some embodiments, the device comprises one or more capture reagents comprising isolated peptides selected from SEQ ID NOs: 28, 98, 141, 145 and combinations thereof. In some embodiments, the device comprises two or more distinct capture reagents, each comprising a different peptide selected from the group consisting of SEQ ID NOs.141, 145, 147, 98, 139 and 56. In some embodiments, the device comprises three or more distinct capture reagents, each comprising a different peptide selected from the group consisting of SEQ ID NOs.141, 145, 147, 98, 139 and 56. In some embodiments, the device comprises four or more distinct capture reagents, each comprising a different peptide selected from the group consisting of SEQ ID NOs.141, 145, 147, 98, 139 and 56. In some embodiments, the device comprises a first capture agent comprising SEQ ID NO:141, a second capture reagent comprising SEQ ID NO:145, a third capture reagent comprising SEQ ID NO: 147; and a fourth capture reagent comprising SEQ ID NO:98.

In some embodiments, the capture reagent is selected from the group consisting of proteins and protein conjugates. In some embodiments, the one or more capture reagents comprise a polypeptide $R_1$—X—$R_2$, wherein X is a peptide selected from the group consisting of SEQ ID NOs.1-149, $R_1$ is selected from the group consisting of the amino terminus of said polypeptide, an amino acid or a polypeptide chain, and $R_2$ is selected from the group consisting of the amino terminus of said polypeptide, an amino acid or a polypeptide chain. In some embodiments, $R_1$ is a polypeptide chain of from about 2 to about 100 amino acids in length. In some embodiments, $R_1$ is a polypeptide chain of from about 2 to about 20 amino acids in length. In some embodiments, $R_2$ is a polypeptide chain of from about 2 to about 100 amino acids in length. In some embodiments, $R_2$ is a polypeptide chain of from about 2 to about 20 amino acids in length.

In some embodiments, the devices further comprise a surface. In some embodiments, the at least one capture reagent is displayed on said surface. In some embodiments, the devices further comprise at least two of said capture reagents arrayed on said surface.

In some embodiments, the immunoassay device is selected from the group consisting of a chip-based array, an ELISA device, a lateral flow device and beads.

In some embodiments, the present invention provides methods of monitoring, detecting or diagnosing infection by *Mycobacterium tuberculosis* in a subject or subjects comprising: contacting an immunoassay device as described above with a biological sample from said subject, and detecting the presence of antibodies in said biological sample that bind to said at least one capture reagent. In some embodiments, the subject is a human. In some embodiments, the subject is a non-human primate. In some embodiments, the sample is a blood or serum sample. In some embodiments, the methods further comprise analyzing multiple biological samples from a non-human primate colony. In some embodiments, the methods further comprise contacting said antibodies in said biological sample that bind to said at least one capture reagent that is detectably labeled for direct or indirect detection. In some embodiments, the detection reagent is labeled with a detectable component selected from the group consisting of a fluorescent compound, a luminescent compound, an enzyme, a radiolabel, and a hapten. In some embodiments, the detection reagent is an antigen binding protein.

In some embodiments, the present invention provides methods of monitoring, detecting or diagnosing infection by *Mycobacterium tuberculosis* in a subject or subjects comprising: detecting the presence of antibodies in a biological sample from said subject or subjects that bind to an antigenic composition comprising a peptide selected from the group consisting of SEQ ID NOs.1-149. In some embodiments, the methods comprise detecting the presence of two or more antibodies in said biological sample that bind two or more antigenic compositions, each comprising a different peptide selected from the group consisting of SEQ ID NOs.1-149. In some embodiments, the methods comprise detecting the presence of three or more antibodies in said biological sample that bind three or more antigenic compositions, each comprising a different peptide selected from the group consisting of SEQ ID NOs.1-149. In some embodiments, the methods comprise detecting the presence of four or more antibodies in said biological sample that bind four or more antigenic compositions, each comprising a different peptide selected from the group consisting of SEQ ID NOs.1-149. In some embodiments, the methods comprise detecting the presence of five or more antibodies in said biological sample that bind five or more antigenic compositions, each comprising a different peptide selected from the group consisting of SEQ ID NOs.1-149. In some embodiments, the methods comprise detecting the presence of ten or more antibodies in said biological sample that bind ten or more antigenic compositions, each comprising a different peptide selected from the group consisting of SEQ ID NOs.1-149.

In some embodiments, antigenic composition is selected from the group consisting of proteins and protein conjugates. In some embodiments, the one or more antigenic compositions comprise a polypeptide $R_1$—X—$R_2$, wherein X is a peptide selected from the group consisting of SEQ ID NOs.1-149, $R_1$ is selected from the group consisting of the amino terminus of said polypeptide, an amino acid or a polypeptide chain, and $R_2$ is selected from the group consisting of the amino terminus of said polypeptide, an amino acid or a polypeptide chain. In some embodiments, $R_1$ is a polypeptide chain of from about 2 to about 100 amino acids in length. In some embodiments, $R_1$ is a polypeptide chain of from about 2 to about 20 amino acids in length. In some embodiments, $R_2$ is a polypeptide chain of from about 2 to about 100 amino acids in length. In some embodiments, $R_2$ is a polypeptide chain of from about 2 to about 20 amino acids in length. In some embodiments, the methods further comprise detecting the presence of antibodies in said sample that bind to at least two different antigenic compositions each comprising a different peptide selected from the group consisting of SEQ ID NOs:141, 145, 147, 98, 139 and 56. In some embodiments, the methods further comprise detecting the presence of antibodies in said sample that bind to at least three different antigenic compositions each comprising a different peptide selected from the group consisting of SEQ ID NOs: 141, 145, 147, 98, 139 and 56. In some embodiments, the methods further comprise detecting the presence of antibodies in said sample that bind to at least four different antigenic compositions each comprising a different peptide selected from the group consisting of SEQ ID NOs: 141, 145, 147, 98, 139 and 56. In some embodiments, the methods further comprise detecting the presence of antibodies in said sample that bind to a first antigenic composition comprising SEQ ID NO:141, a second antigenic composition comprising SEQ ID NO:145, a third antigenic composition comprising SEQ ID NO: 147; and a fourth antigenic composition comprising SEQ ID NO:98. In some embodiments, the methods further comprise detecting the presence of antibodies in said sample that bind to a fifth antigenic composition comprising SEQ ID NO:139 and a sixth antigenic agent comprising SEQ ID NO:56.

In some embodiments, the at least one antigenic composition is displayed on a device comprising a surface. In some embodiments, at least two of said antigenic compositions are arrayed on said surface. In some embodiments, the surface is a component of a device selected from the group consisting of a chip-based array, an ELISA device, a lateral flow device and beads.

In some embodiments, the method has a specificity of greater than about 80%. In some embodiments, the method has a specificity of greater than about 90%. In some embodiments, the method has a specificity of greater than about 95%. In some embodiments, the method has a sensitivity of greater than about 80%. In some embodiments, the method has a sensitivity of greater than about 90%. In some embodiments, the method has a sensitivity of greater than about 95%.

In some embodiments, the present invention provides a panel of antigenic compositions comprising two or more antigenic compositions, each comprising a different peptide selected from the group consisting of SEQ ID NOs.1-149.

In some embodiments, the present invention provides an immunogenic composition comprising one more peptides selected from the group consisting of peptides identified by SEQ ID NOs:1-149. In some embodiments, the immunogenic compositions further comprise an adjuvant. In some embodiments, the immunogenic compositions comprise a fusion polypeptide comprising two or more peptides identified by SEQ ID NOs:1-149.

In some embodiments, the present invention provides methods of vaccinating a subject comprising administering the immunogenic composition at described above to a subject.

In some embodiments, the present invention provides for the use of the assay devices described above to detect, monitor or diagnose infection or exposure to *Mycobacterium tuberculosis* in a subject or subjects, particularly a non-human primate or a colony of non-human primates.

In some embodiments, the present invention provides for the use of the immunogenic compositions described above to detect, monitor or diagnose infection or exposure to *Mycobacterium tuberculosis* in a subject or subjects, particularly a non-human primate or a colony of non-human primates.

In some embodiments, the present invention provides for the use of immunogenic compositions described above to vaccinate a subject or subjects, particularly a non-human primate or a colony of non-human primates.

In some embodiments, the one or more of the peptides or conjugates described above (alone or in combination) are used as an antigen stimulation mixture for cell based assays including, but not limited to, cytokine release assays (particularly interferon gamma release and interleukin 12) as measured by ELISA, Elispot, or bead based methods. In other embodiments, the peptides or conjugates described above (alone or in combination) are used in T-cell capture assays. In still other embodiments, the peptides or conjugates described above (alone or in combination) are used as an antigenic substitute for tuberculin in the tuberculin skin test (TST).

DESCRIPTION OF THE FIGURES

FIG. 3 The Relative Intensity Unit (RIU) is reported for the Mix of peptides (Peptides 6, 15, 17, and 20) and for each peptide individually. Values highlighted in grey show higher signal than the Naïve pooled sample.

DEFINITIONS

Figure 1:
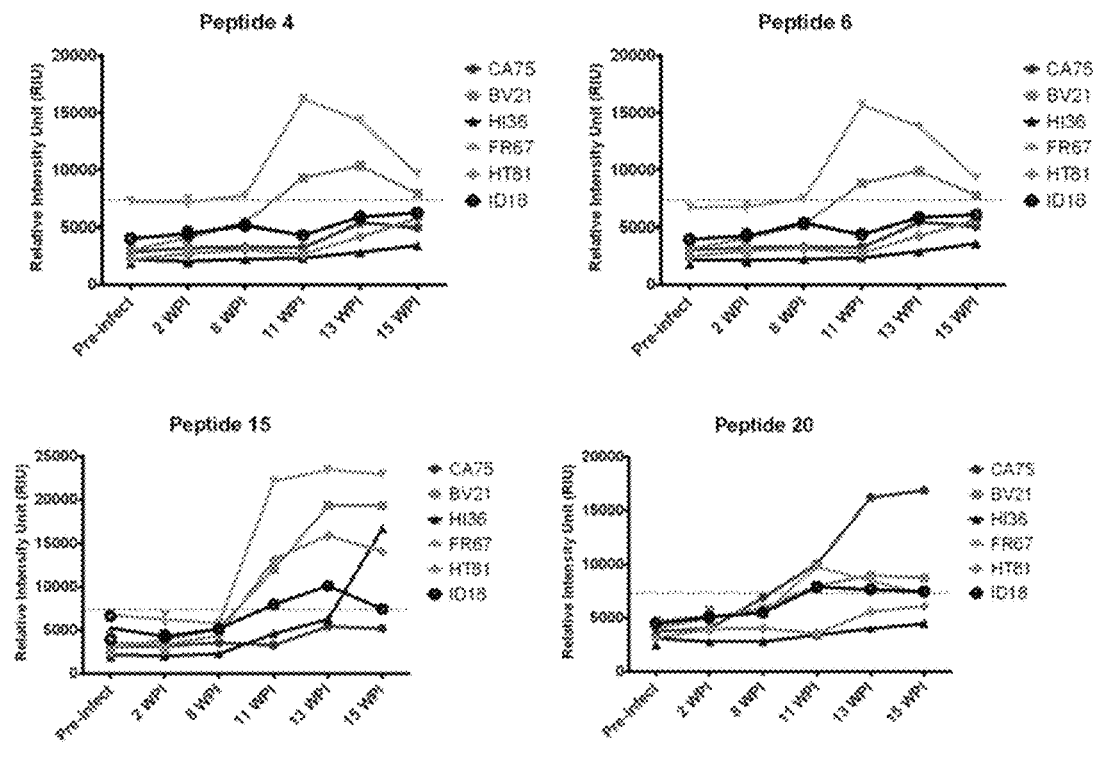
FIG. 1 provides an analysis of positive and negative serum samples from Tulane National Primate Research Center (time course infection study) using a multiplexed Ag microarray with individual and mixed peptide-BSA conjugates. A: Peptide 4; B: Peptide 6; C: Peptide 15; D: Peptide 20; E: Mix A.
Figure 1:
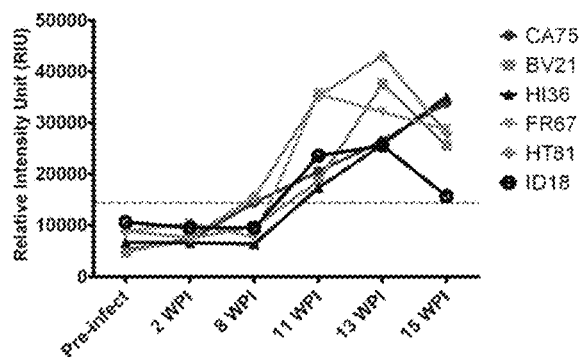
Figure 2:
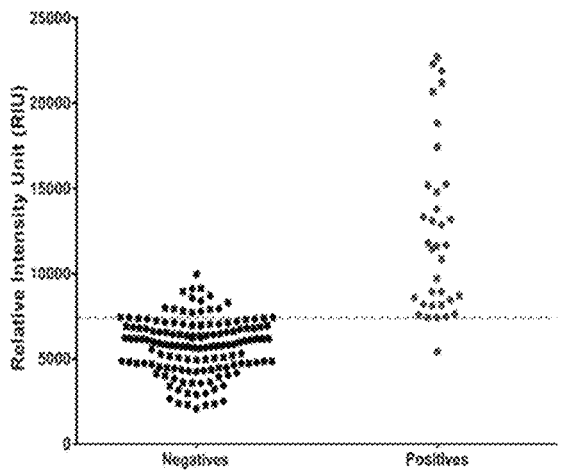
FIG. 2 provides an ROC analysis of 141 negative and 35 positive serum samples.

The terms "detecting" or "detection" or "determining the level" refer to quantitatively or non-quantitatively determination of the presence of the analyte(s) under investigation (e.g., AMH). "Detecting Formation of a Complex" refers to detecting a complex comprising a detector reagent by any method suitable for observing the particular label associated with the detector reagent; for instance, visual observation of a colored (or otherwise visible) label, measurement or visual detection of a fluorescent, chemiluminescent or radioactive label.

As used herein, the term "sample" is used in its broadest sense. In one sense, it is meant to include a specimen or culture obtained from any source, as well as biological and environmental samples. Biological samples may be obtained from animals (including humans) and encompass fluids, solids, tissues, and gases. Biological samples include urine and blood products, such as plasma, serum and the like. Such examples are not however to be construed as limiting the sample types applicable to the present invention.

As used herein, the terms "protein," "polypeptide," and "peptide" refer to a molecule comprising amino acids joined via peptide bonds. In general "peptide" is used to refer to a sequence of 20 or less amino acids and "polypeptide" is used to refer to a sequence of greater than 20 amino acids. The proteins, polypeptides and peptides may be natural, produced by a recombinant process (i.e., expression of exogenous nucleic acid encoding the peptide, polypeptide or protein in an organism, host cell, or cell-free system) or produced by chemical synthesis.

The term "carrier" refers to a molecule that allows conjugation of additional, usually smaller, molecules such as peptides.

The term "specific binding partner (or binding partner)" refers to a member of a pair of molecules that interact by means of specific, noncovalent interactions that depend on the three-dimensional structures of the molecules involved. Typical pairs of specific binding partners include antigen/ antibody, hapten/antibody, hormone/receptor, nucleic acid strand/complementary nucleic acid strand, substrate/enzyme, inhibitor/enzyme, carbohydrate/lectin, biotin/(strept) avidin, and virus/cellular receptor.

As used herein, the terms "immunoglobulin" or "antibody" refer to proteins that bind a specific antigen. Immunoglobulins include, but are not limited to, polyclonal, monoclonal, chimeric, and humanized antibodies, Fab fragments, F(ab')2 fragments, and includes immunoglobulins of the following classes: IgG, IgA, IgM, IgD, IbE, and secreted immunoglobulins (sIg). Immunoglobulins generally comprise two identical heavy chains and two light chains. However, the terms "antibody" and "immunoglobulin" also encompass single chain antibodies and two chain antibodies.

The term "label" refers to a molecule or composition bound to an analyte, analyte analog, detector reagent, or binding partner that is detectable by spectroscopic, photochemical, biochemical, immunochemical, electrical, optical or chemical means. Examples of labels, including enzymes, colloidal gold particles, colored latex particles, have been disclosed (U.S. Pat. Nos. 4,275,149; 4,313,734; 4,373,932; and 4,954,452, each incorporated by reference herein). Additional examples of useful labels include, without limitation, radioactive isotopes, co-factors, ligands, chemiluminescent or fluorescent agents, protein-adsorbed silver particles, protein-adsorbed iron particles, protein-adsorbed copper particles, protein-adsorbed selenium particles, protein-adsorbed sulfur particles, protein-adsorbed tellurium particles, protein-adsorbed carbon particles, and protein-coupled dye sacs. The attachment of a compound (e.g., a detector reagent) to a label can be through covalent bonds, adsorption processes, hydrophobic and/or electrostatic bonds, as in chelates and the like, or combinations of these bonds and interactions and/or may involve a linking group.

The phrase "label-free detection" refers to the detection of an immunoglobulin or antibody without the addition of a label to the immunoglobulin or a primary or secondary affinity binder that contains a label. Examples of label-free detection may be Surface Plasmon Resonance (SPR), Quartz Crystal Microbalance (QCM), and Optical Interferometry.

The phrase "specifically binds to an analyte" or "specifically immunoreactive with," when referring to an antibody or polypeptide, refers to a binding reaction which is determinative of the presence of the analyte (which can be an antibody or polypeptide) in the presence of a heterogeneous population of molecules such as proteins and other biologic molecules. Thus, under designated immunoassay conditions, the specified antibodies or polypeptides bind to a particular analyte and do not bind in a significant amount to other analytes present in the sample. A variety of immunoassay formats may be used to select antibodies or polypeptides specifically immunoreactive with a particular analyte. For example, solid-phase ELISA immunoassays are routinely used to select monoclonal antibodies polypeptides specifically immunoreactive with a protein or antibody See Harlow and Lane, Antibodies, A Laboratory Manual, CSHP, New York (1988), for a description of immunoassay formats and conditions that can be used to determine specific immunoreactivity.

The term "capture agent" refers to an unlabeled specific binding partner that is specific for (i) an analyte, such as an immunoglobulin that has been produced by an animal in response to infection by *Mycobacterium tuberculosis*, or (ii) a detector reagent or an analyte, as in a competitive assay, or for (iii) an ancillary specific binding partner, which itself is specific for the analyte, as in an indirect assay. As used herein, an "ancillary specific binding partner" is a specific binding partner that binds to the specific binding partner of an analyte. For example, an ancillary specific binding partner may include an antibody specific for another antibody, for example, goat anti-human antibody. A "capture area" is a region of a lateral flow device where the capture reagent is immobilized. A lateral flow device may have more than one capture area, for example, a "primary capture area," a "secondary capture area," and so on. Often a different capture reagent will be immobilized in the primary, secondary, or other capture areas. Multiple capture areas may have any orientation with respect to each other on the lateral flow substrate; for example, a primary capture area may be distal or proximal to a secondary (or other) capture area and vice versa. Alternatively, a primary capture area and a secondary (or other) capture area may be oriented perpendicularly to each other such that the two (or more) capture areas form a cross or a plus sign or other symbol.

The term "detector reagent" refers to a specific binding partner that is conjugated to a label. Detector reagents include, for example, labeled analyte-specific binding members or labeled ancillary specific binding members (such as enzyme-conjugate, goat anti-primate antibodies).

The term "lateral flow device" refers to an analytical device in the form of a test strip used in lateral flow chromatography, in which a test sample fluid, suspected of containing an analyte, flows (for example by capillary action) through the strip (which is frequently made of bibulous materials such as paper, nitrocellulose, and cellulose). The test fluid and any suspended analyte can flow along the strip to a detection zone in which the analyte (if present) interacts with a detection agent to indicate a presence, absence and/or quantity of the analyte.

The term "sample application area" refers to an area where a fluid sample is introduced to an immunochromatographic test strip, such as an immunochromatographic test strip present in a lateral flow device. In one example, the sample may be introduced to the sample application area by external application, as with a dropper or other applicator. In another example, the sample application area may be directly immersed in the sample, such as when a test strip is dipped into a container holding a sample. In yet another example, the sample may be poured or expressed onto the sample application area.

The term "solid support" or "substrate" means material which is insoluble, or can be made insoluble by a subsequent reaction. Numerous and varied solid supports are known to those in the art and include, without limitation, nitrocellulose, the walls of wells of a reaction tray, multi-well plates, test tubes, polystyrene beads, magnetic beads, membranes, microparticles (such as latex particles), and sheep (or other animal) red blood cells. Any suitable porous material with sufficient porosity to allow access by detector reagents and a suitable surface affinity to immobilize capture reagents is contemplated by this term. For example, the porous structure of nitrocellulose has excellent absorption and adsorption qualities for a wide variety of reagents, for instance, capture reagents. Nylon possesses similar characteristics and is also suitable. Microporous structures are useful, as are materials with gel structure in the hydrated state.

Further examples of useful solid supports include: natural polymeric carbohydrates and their synthetically modified, cross-linked or substituted derivatives, such as agar, agarose, cross-linked alginic acid, substituted and cross-linked guar gums, cellulose esters, especially with nitric acid and carboxylic acids, mixed cellulose esters, and cellulose ethers; natural polymers containing nitrogen, such as proteins and derivatives, including cross-linked or modified gelatins;

natural hydrocarbon polymers, such as latex and rubber; synthetic polymers which may be prepared with suitably porous structures, such as vinyl polymers, including polyethylene, polypropylene, polystyrene, polyvinylchloride, polyvinylacetate and its partially hydrolyzed derivatives, polyacrylamides, polymethacrylates, copolymers and terpolymers of the above polycondensates, such as polyesters, polyamides, and other polymers, such as polyurethanes or polyepoxides; porous inorganic materials such as sulfates or carbonates of alkaline earth metals and magnesium, including barium sulfate, calcium sulfate, calcium carbonate, silicates of alkali and alkaline earth metals, aluminum and magnesium; and aluminum or silicon oxides or hydrates, such as clays, alumina, talc, kaolin, zeolite, silica gel, or glass (these materials may be used as filters with the above polymeric materials); and mixtures or copolymers of the above classes, such as graft copolymers obtained by initializing polymerization of synthetic polymers on a pre-existing natural polymer.

It is contemplated that porous solid supports, such as nitrocellulose, described hereinabove are preferably in the form of sheets or strips. The thickness of such sheets or strips may vary within wide limits, for example, from about 0.01 to 0.5 mm, from about 0.02 to 0.45 mm, from about 0.05 to 0.3 mm, from about 0.075 to 0.25 mm, from about 0.1 to 0.2 mm, or from about 0.11 to 0.15 mm. The pore size of such sheets or strips may similarly vary within wide limits, for example from about 0.025 to 15 microns, or more specifically from about 0.1 to 3 microns; however, pore size is not intended to be a limiting factor in selection of the solid support. The flow rate of a solid support, where applicable, can also vary within wide limits, for example from about 12.5 to 90 sec/cm (i.e., 50 to 300 sec/4 cm), about 22.5 to 62.5 sec/cm (i.e., 90 to 250 sec/4 cm), about 25 to 62.5 sec/cm (i.e., 100 to 250 sec/4 cm), about 37.5 to 62.5 sec/cm (i.e., 150 to 250 sec/4 cm), or about 50 to 62.5 sec/cm (i.e., 200 to 250 sec/4 cm). In specific embodiments of devices described herein, the flow rate is about 62.5 sec/cm (i.e., 250 sec/4 cm). In other specific embodiments of devices described herein, the flow rate is about 37.5 sec/cm (i.e., 150 sec/4 cm).

The surface of a solid support may be activated by chemical processes that cause covalent linkage of an agent (e.g., a capture reagent) to the support. However, any other suitable method may be used for immobilizing an agent (e.g., a capture reagent) to a solid support including, without limitation, ionic interactions, hydrophobic interactions, covalent interactions and the like. The particular forces that result in immobilization of an agent on a solid phase are not important for the methods and devices described herein.

Except as otherwise physically constrained, a solid support may be used in any suitable shapes, such as films, sheets, strips, or plates, or it may be coated onto or bonded or laminated to appropriate inert carriers, such as paper, glass, plastic films, or fabrics.

A "lateral flow substrate" is any solid support or substrate that is useful in a lateral flow device.

The term "Western blot" refers to the analysis of protein(s) (or polypeptides) immobilized onto a support such as nitrocellulose or a membrane. The proteins are run on acrylamide gels to separate the proteins, followed by transfer of the protein from the gel to a solid support, such as nitrocellulose or a nylon membrane. The immobilized proteins are then exposed to antibodies with reactivity against an antigen of interest. The binding of the antibodies may be detected by various methods, including the use of radiolabeled antibodies.

As used herein, the terms "protein microarray" and "protein chip" refer to protein-detecting molecules immobilized at high density on a substrate, and probed for various biochemical activities. (See, for example: Zhu H and Snyder M, "Protein chip technology", Current Opinion in Chemical Biology 7: 55-63, 2003; Cutler P, "Protein arrays: The current state of the art", Proteomics 3; 3-18, 2003; and MacBeath G, "Protein microarrays and proteomics", Nature Genetics Supplement 32: 526-532, 2002, each of which is incorporated herein by reference in its entirety).

As used herein, the term "sensitivity" when used in reference to an assay refers to the proportion of actual positives which are correctly identified as such (e.g., the percentage of infected, latent or symptomatic subjects who are correctly identified as having the condition). Sensitivity may be calculated as the number of true positives divided by the sum of the number of true positives and the number of false negatives.

As used herein the term "specificity" when used in relation to an assay refers to proportion of negatives which are correctly identified (e.g., the percentage of healthy subjects who are correctly identified as not having the condition). Specificity may be calculated as the number of true negatives divided by the sum of the number of true negatives and the number of false positives.

"Blocking agent" means a molecular arrangement that will absorb to the surface of the substrate. The absorption can result because of non-covalent bonding attractive forces or because the blocking agent contains a reactive group. For example, a polyethylene glycol group can act as a blocking agent when it is covalently bonded to the surface or the protein bovine serum albumin can act as a blocking agent when it is non-covalently attached to the surface.

"Fusion protein" means a protein that contains additional molecular arrangements including, but not limited to, naturally or non-naturally amino acids usually the result of producing the protein by manipulating biological processes.

"Linker" means a molecular arrangement with a reactive group that binds a biological entity by exposure to the reactive group resulting in a biological entity linked to the molecular arrangement. The linker includes the molecular arrangements before and after the reactive group binds to the biological entity.

DETAILED DESCRIPTION OF THE INVENTION

The present invention relates to novel peptides that may be used in whole or in combination for the detection of *Mycobacterium tuberculosis* and related infections, including *Mycobacterium bovis*. In particular, the present invention relates to compositions and methods involving detection of antibodies contained in the blood of human or non-human primates that arise from an infection from *M. tuberculosis* or vaccination using an epitope specific inoculation. More particularly, the present invention provides a means to distinguish early, active, and latent *M. tuberculosis* infection. More particularly, the present invention describes an immunological diagnostic mechanism for the detection of *M. tuberculosis* infection.

Historically, antigens used for TB immunoassays in non-human primates have focused on secreted antigens that have been shown to have diagnostic potential in humans. Work by Brusasca et al. first used 14 proteins identified as immunodominant in human TB to identify the antibody response to these proteins in experimentally infected NHPs[23]. Of these 14, only 3 proteins (ESAT-6, α-crystallin, and CFP-10)

identified antibodies in more than 85% of infected animals with an antibody reaction. Importantly, the most seroreactive human antigen at the time of that study (38 kDa, Rv0934) was only reactive with 14% of infected animals, highlighting the need for NHP specific antigen discovery. More recent studies have shown that individual recombinant proteins previous used in commercial immunochromatographic kits for both human and NHPs have at best 75% diagnostic sensitivity, and several TST positive animals were seronegative to the panel of 10 recombinant proteins [24]. Our preliminary studies showed that neither purified recombinant proteins (ESAT-6 and 16 kDa α-crystallin) nor the heterogeneous TST antigen MOT were able to accurately distinguish between positive and negative samples in our microarray based assay for antibody detection. Overall, current TB tests are limited by the poorly defined antigens for NHP testing and cannot use those antigens successfully in humans.

Accordingly, the present invention provides individual peptides, polypeptides, and proteins as well as panels of peptides, polypeptides, and proteins which are useful detecting, monitoring or diagnosing infection by *Mycobacterium tuberculosis* and for making vaccines to protect against infection by *Mycobacterium tuberculosis*. In some embodiments, the peptides, proteins, or polypeptides are encoded by or comprise SEQ ID Nos.: 1-149 or are at least 80%, 90%, 95% or 99% identical to SEQ ID NOs.: 1-149 and have the property of binding to an antibody that recognizes the corresponding unaltered sequence.

| Sequence ID | Peptide Sequence | |
|---|---|---|
| 1 | AAATHSPRNVQFYCI | |
| 2 | AAIPLLTAPVIGMAM | |
| 3 | AAQVWSQCHSYGFDA | |
| 4 | ADEEQQQALSSQMGF | |
| 5 | AFEWYYQSGLSIVMP | |
| 6 | AIGLGGGAGGDGGQG | |
| 7 | AKLIIWYPHYAWLLL | |
| 8 | AMEDLVRAYHAMSST | |
| 9 | ANNWYQPARRGFSTG | |
| 10 | APAPIASPIPVGAPG | |
| 11 | AREVVELDRDEAMRL | |
| 12 | ASQSTTNPIFGMPSP | |
| 13 | ASVSIDGAQQASVAL | |
| 14 | DAERFGARLVASPQH | |
| 15 | DALAGKGASAIVLRG | |
| 16 | DGITLFNPAAVPIRR | |
| 17 | DGTHQTLQGADLTVI | Peptide 2 |
| 18 | DQDTAELHRRATHFR | |
| 19 | DVSVAQGVTNLHTAI | |
| 20 | DYAIVGGAPGSAPRE | |
| 21 | EARRADLGCDIVDAT | |
| 22 | EFPDLEGQVQDLAAQ | |
| 23 | EGLWAGVVIPESGRA | |
| 24 | ESPAPHVPSHGPHQP | |
| 25 | FDETIDKSTDKTLHS | |
| 26 | FDWRYPPSPPPQPTQ | |
| 27 | FLIIDGWPGFVGEFP | |
| 28 | FPQYRELGVYLVRGI | Peptide 4 |
| 29 | FQIHDPTTKDRQGND | |
| 30 | FSIVRRSSRPEPSPR | |
| 31 | GAGGSLTRTPLMSQL | |
| 32 | GAGSGFANFGSLGSG | |
| 33 | GCGTCNIAEALKMSL | |
| 34 | GDFYAGEKSMTLDRA | |
| 35 | GFDFTAQGVWAFARP | |
| 36 | GGAPQTGKSTLLQTM | |
| 37 | GGARFAVEQGHGVAL | |
| 38 | GGREGPTAQISAGFC | |
| 39 | GIAFGLFIVTNAAKL | |
| 40 | GLDPVNYQNFAVTND | |
| 41 | GLYNTGGLPPGTPAV | |
| 42 | GNAGLFGDGGAGGDG | |
| 43 | GPSIQARLRAEEASG | |
| 44 | GRGAPEDAPLIMRGK | |
| 45 | GTTQFGDTTANKDAW | |
| 46 | HLAKGELRSIHNRTD | |
| 47 | HLREKGVKLEAQRPH | |
| 48 | HRHPSANQQMLWTLV | |
| 49 | HVKPTGSAVVGLSMA | |
| 50 | HYLHVRPADQFDAMI | |
| Si | IELTKRTLWSGLDAA | |
| 52 | ILLECTMAGMATCTL | |
| 53 | IPIGLRETDLTPAHC | |
| 54 | ITYQAWQAQWNQAME | |
| 55 | IVGAAGGMPPMAPLA | |
| 56 | KGRSSEMIICGGVNI | Peptide 9 |
| 57 | KVKPQKPKATKPPKV | |
| 58 | KYVEADLRVLDEIAP | |

| Sequence ID | Peptide Sequence | |
|---|---|---|
| 59 | LAAPVDPSTPAPSTT | |
| 60 | LAIPGTNWIGQAAEA | |
| 61 | LDWERNFLRQLQSHR | |
| 62 | LGGGVAANLGRAASV | |
| 63 | LGNSVYTSNAQLVVY | Peptide 10 |
| 64 | LGQPRSYLAPPTRPA | |
| 65 | LLSQGKFPYKSSWIE | |
| 66 | LNTARLMAGAGPAPM | |
| 67 | LPGTAVANPVDPARI | |
| 68 | LQVIERTWRYLKVPC | |
| 69 | LRCGDFALGGPQGRG | |
| 70 | LRILKTDIYAPTGAV | Peptide 11 |
| 71 | LTYWTAGDTRNRGRE | |
| 72 | MAGDTTITIVGNLTA | |
| 73 | MASGSGLCKTTSNFI | |
| 74 | MELLDAFGIAMAGAP | |
| 75 | MGTTLTAILFAGNRL | |
| 76 | MIDGVYKVCKGLEKI | |
| 77 | MKLTTMIKTAVAVVA | Peptide 12 |
| 78 | MNSAIIKIAKWAQSQ | |
| 79 | MQLVDRVRGAVTGMS | |
| 80 | MRLSLTALSAGVGAV | |
| 81 | MSAPAVAAGPTAAGA | |
| 82 | NAEIAATIANGGITM | |
| 83 | NARTADGINYRVLWQ | |
| 84 | NDPDRASMLFEGSTI | |
| 85 | NKPVISWAGDNGIYF | |
| 86 | NVDGAQREIDILEND | |
| 87 | NVDGAQREIDILEND | |
| 88 | PANRPGRAVSMEKHH | |
| 89 | PLDDGDVIDSMFMSK | |
| 90 | PLQALQTVQQNVLTV | |
| 91 | PPAATQTLGQLGEMS | |
| 92 | PPGDERHMLWFELMK | |
| 93 | PPIRAPGGDAADTRL | |
| 94 | PPTPPMPIAGPEPAP | |
| 95 | PSGGPVAASAAPSIP | |
| 96 | PSGTAVGAGARSSVG | |

| Sequence ID | Peptide Sequence | |
|---|---|---|
| 97 | QAQLISSQAQQGGQQ | |
| 98 | QEAGNFERISGDLKT | Peptide 20 |
| 99 | QMQDAFETGVMFSLH | |
| 100 | QSGPAHADESAASVT | |
| 101 | RGIPPGHVGVAWRGT | |
| 102 | RNIIDMHLPRHRLDS | |
| 103 | RQRRTKGAGGSFTSR | |
| 104 | RRHLQDVWGVDVSGA | Peptide 14 |
| 105 | RSEPDKVNRVVAEMQ | |
| 106 | RTYSQIDDGAAGVFA | |
| 107 | SAASVTPAAASGVPG | |
| 108 | SADDGTPVSMIPVSA | |
| 109 | SAKMLSVVPLMAGGG | |
| 110 | SDVFTTITPATAQGI | |
| 111 | SKAATDMLAYQYHKS | |
| 112 | SKIPRGEEAGKLWDA | |
| 113 | SKLMTRIAGAGAMGS | |
| 114 | SLFPEFSELFAAFPS | |
| 115 | SMEKHHLMIGVPRFD | |
| 116 | SPGQQPGGGVPAQAM | |
| 117 | SQRGWRHWVHALTRI | |
| 118 | SSTHEANTMAMMARD | |
| 119 | STVSGVVVVASVSID | |
| 120 | TASDFWGGAGSAACQ | |
| 121 | TDAKLLSSILTYHVI | |
| 122 | TGQGNSLKVGNADVV | |
| 123 | TLLQTMVMSAAATHS | |
| 124 | TMLVVPVGAGPGLRE | |
| 125 | TNAAKLTVAVARIAL | |
| 126 | TPKTKIETALDRQKI | |
| 127 | TQAVLTATNFFGINT | |
| 128 | TRDKFLSAATSSTPR | |
| 129 | TRLMRLEDEMKEGRY | |
| 130 | TRQLHQLGLESSERE | |
| 131 | TTGPKPLVQDEYAKH | |
| 132 | TYSQIDDGAAGVFAE | |
| 133 | VHLARDLRLHRDVAV | |
| 134 | VLDESPEFDRTALNR | |

-continued

| Sequence ID | Peptide Sequence | |
|---|---|---|
| 135 | VLESKTVGDSCVVLE | |
| 136 | VTSLFSQVGGTGGGN | |
| 137 | VVVGGSIDAAIDTAK | |
| 138 | APHESFDTQYTRHVE | Peptide 1 |
| 139 | EAEHQAIISDVLTAS | Peptide 3 |
| 140 | HARDVLADRRLFVLT | Peptide 5 |
| 141 | IHSLLDEGKQSLTKLAAAWGGSGSEAY | Peptide 6 |
| 142 | KELHLRLGTATADLS | Peptide 7 |
| 143 | KFRQLGDIVLELAAA | Peptide 8 |
| 144 | NSLVTATHGANVSLV | Peptide 13 |
| 145 | TKLAAAWGGSGSEAYQGVQQKWDATAT | Peptide 15 |
| 146 | VWRRDLRAIVRLLAW | Peptide 16 |
| 147 | APRADLATREEQIAV | Peptide 17 |
| 148 | HDIQVTLSAGQSVTL | Peptide 18 |
| 149 | IRTNQVSTILASDGS | Peptide 19 |

SEQ ID NOs.: 1-149 encode peptide sequences that serve as antigens when a subject is infected by *Mycobacterium tuberculosis* or related organisms. The present invention encompasses these peptides in isolation as well as proteins, polypeptides, fusion proteins and protein conjugates that comprise the identified peptide sequences. In preferred embodiments, the proteins, polypeptides, fusion proteins and protein conjugates that comprise one or more of SEQ ID NOs:1-149 have the property of binding to antibodies that specifically recognize peptides encoded by SEQ ID NOs:1-149. In some embodiments, polypeptides comprising a peptide (or peptides) encoded by SEQ ID NOs: 1-149 comprise the base peptide and from 1, 2, 5, 10, 20, 30, 40, or 50 to about 100 or 200 amino acids on either or both of the amino- or carboxy-terminus of the base peptide. In some embodiments, polypeptides comprising a peptide (or peptides) encoded by SEQ ID NOs: 1-149 comprise the base peptide and 1, 2, 5, at least 5, at least 10, at least 20, at least 30, at least 40, or at least 50 amino acids on either or both of the amino- or carboxy-terminus of the base peptide.

In some embodiments, the present invention provides devices, kits and methods for determining whether a subject has been exposed to *Mycobacterium tuberculosis* or related organisms, infected by *Mycobacterium tuberculosis* or related organisms or has tuberculosis or other disease. In some embodiments, the subject is a human or non-human primate. In some embodiments, the methods, kits and devices are used to assay the presence or amount of antibodies in the serum, blood or tissue of a subject to specified *Mycobacterium tuberculosis* peptides. A number of methods and devices can be used to assay samples from subjects for the presence of antibodies to *Mycobacterium tuberculosis* (*M. tb*), including, but not limited to, protein detection chips, bead-based assays, lateral flow devices, and enzyme-linked immunosorbent assays (ELISAs). The assays may be single-plex assays or multiplex assays.

In singleplex assays, an antigenic composition or capture reagent comprising one of the peptides encoded by SEQ ID NOs:1-149 is utilized in the assay. In some embodiments, the capture reagent comprises an isolated peptide encoded by one of by SEQ ID NOs:1-149. For example, the capture reagent may comprise the isolated peptide in addition to a conjugate or linker molecule. In some embodiments, the isolated base peptide may be flanked by from 1, 2, 5, 10, 20, 30, 40, or 50 to about 100 or 200 amino acids on either or both of the amino- or carboxy-terminus of the base peptide. In multiplex assays, a panel of antigenic compositions or capture reagents are utilized in the assay. In some embodiments, the panel comprises at least 2, 3, 5, 5, 6, 7, 8, 9, 10, 11, 12, 13, 14, 15, 16, 17, 18, 19, 20, 25, 30, 40, 50, 60, 70, 80, 90 or 100 or more of SEQ ID NOs: 1-149. In some embodiments, the panel comprises 2, 3, 5, 5, 6, 7, 8, 9, 10, 11, 12, 13, 14, 15, 16, 17, 18, 19, 20, 25, 30, 40, 50, 60, 70, 80, 90 or 100 of SEQ ID NOs: 1-149. In some embodiments, the specific capture reagents utilized in the multiplex assay comprise an isolated peptide encoded by one of by SEQ ID NOs:1-149. For example, the capture reagent may comprise the isolated peptide in addition to a conjugate or linker molecule. In some embodiments, the isolated base peptide may be flanked by from 1, 2, 5, 10, 20, 30, 40, or 50 to about 100 or 200 amino acids on either or both of the amino- or carboxy-terminus of the base peptide. In some embodiments, the assays have a specificity of at least 80%, 90%, 95% or 99%. In some embodiments, the assays have a sensitivity of at least 80%, 90%, 95% or 99%. In some embodiments, the present invention provides an antigenic composition or capture reagent comprising one of the peptides encoded by SEQ ID NOs:1-149 that is conjugated to a carrier molecule.

In some embodiments, the *M. tb* capture reagent of antigenic composition is brought in contact with, and allowed to bind to, a solid support or carrier, such as nitrocellulose or polystyrene or any other solid support known in the art (see below), allowing the antigens to adsorb and become immobilized to the solid support. This immobilized antigen is then allowed to interact with the biological fluid sample which is being tested for the presence of anti-*M. tb* antibodies, such that any antibodies in the sample will bind to the immobilized antigen. The support to which the antibody is now bound may then be washed with suitable buffers after which a detectably labeled binding partner for the antibody is introduced. The binding partner binds to the immobilized antibody. Detection of the label is a measure of the immobilized antibody. In some embodiments, the immunoassay of this invention may be a "two-site" or "sandwich" assay. The fluid containing the antibody being assayed is allowed to contact a solid support. After addition of the *M. tb* antigen(s), a quantity of detectably labeled soluble antibody is added to permit detection and/or quantitation of the ternary complex formed between solid-phase antibody, antigen, and labeled antibody. Sandwich assays are described by Wide, Radioimmune Assay Method, Kirkham et al, Eds., E. & S. Livingstone, Edinburgh, 1970, pp 199-206.

A preferred binding partner for these assays is an anti-immunoglobulin antibody ("second antibody") produced in a different species. Thus to detect a nonhuman primate antibody, a detectably labeled goat anti-simian immunoglobulin "second" antibody may be used. The solid phase support may then be washed with the buffer a second time to remove unbound antibody. The amount of bound label on the solid support may then be detected by conventional means appropriate to the type of label used (see below).

Such a "second antibody" may be specific for epitopes characteristic of a particular human immunoglobulin isotype, for example IgM, IgG$_1$, IgG$_{2a}$, IgA and the like, thus permitting identification of the isotype or isotypes of antibodies in the sample which are specific for the *M. tb* antigen. Alternatively, the second antibody may be specific for an idiotype of the anti-*M. tb* antibody of the sample.

As alternative binding partners for detection of the sample antibody, other known binding partners for human immunoglobulins may be used. Examples are the staphylococcal immunoglobulin binding proteins, the best know of which is protein A. Also intended is staphylococcal protein G, or a recombinant fusion protein between protein A and protein G. Protein G of group G and group C streptococci binds to the Fc portion of Ig molecules as well as to IgG Fab fragment at the $V_{H3}$ domain. Protein C of *Peptococcus magnus* binds to the Fab region of the immunoglobulin molecule. Any other microbial immunoglobulin binding proteins, for example from Streptococci, are also intended (for example, Langone, J. J., Adv. Immunol 32:157 (1982)).

In another embodiment of this invention, a biological fluid suspected of containing antibodies specific for *M. tb* antigens may be brought into contact with a solid support or carrier which is capable of immobilizing soluble proteins. The support may then be washed with suitable buffers followed by treatment with *M. tb* antigens reagent, which may be detectably labeled. Bound antigen is then measured by measuring the immobilized detectable label. If the *M. tb* antigen reagent is not directly detectably labeled, a second reagent comprising a detectably labeled binding partner for the *M. tb* antigen, generally a second anti-*M. tb* antibody such as a murine mAb, is allowed to bind to any immobilized antigen. The solid phase support may then be washed with buffer a second time to remove unbound antibody. The amount of bound label on said solid support may then be detected by conventional means.

By "solid phase support" or carrier is intended any support capable of binding a proteinaceous antigen or antibody molecules or other binding partners according to the present invention. Well-known supports, or carriers, include glass, polystyrene, polypropylene, polyethylene, polyvinylidene difluoride, dextran, nylon, magnetic beads, amylases, natural and modified celluloses, polyacrylamides, agaroses, and magnetite. The nature of the carrier can be either soluble to some extent or insoluble for the purposes of the present invention. The support material may have virtually any possible structural configuration so long as it is capable of binding to an antigen or antibody. Thus, the support configuration may be spherical, as in a bead, or cylindrical, as in the inside surface of a test tube, or the external surface of a rod. Alternatively, the surface may be flat such as a sheet, test strip, etc. Preferred supports include polystyrene beads, 96-well polystyrene microplates and test strips, all well-known in the art. Those skilled in the art will know many other suitable carriers for binding antibody or antigen, or will be able to ascertain the same by use of routine experimentation.

Using any of the assays described herein, those skilled in the art will be able to determine operative and optimal assay conditions for each determination by employing routine experimentation. Furthermore, other steps as washing, stirring, shaking, filtering and the like may be added to the assays as is customary or necessary for the particular situation.

In some embodiments, the present invention provides protein chip assays comprising one or more capture reagents or antigenic compositions comprising at least one of SEQ ID NOs:1-149. In such an assay, the capture reagents or antigenic compositions are immobilized on a solid support such as a chip. In some embodiments, the protein chip assay utilizes a solid support coated with ultrathin or clear nitrocellulose. See, e.g., US PAT PUBL. 20090253586 and 20090075828, both of which are incorporated herein by reference in their entirety. In preferred embodiments, the capture reagents or antigenic compositions are arrayed on the solid support. In multiplexed assays, a panel of capture reagents or antigenic compositions as described above is arrayed on the solid support. See, e.g., US PAT PUBL. 20090253586 and 20090075828, both of which are incorporated herein by reference in their entirety. A sample from a subject is passed over the solid support. Bound antibodies from the sample are then detected using any suitable method. Other suitable protein chip assays are described, for example, in U.S. Pat. Nos. 6,197,599; 6,294,790 and US Patent Application US20010014461A1, each of which is herein incorporated by reference in its entirety).

In some embodiments, a cytometric bead array assay is used (Quantum Plex kit, Bangs Laboratories; Cytometric Bead Array kit, BD Biosciences). These systems allow for multiple analyte detection with small volume samples. In other embodiments, a LUMINEX bead assay is used. See, e.g., U.S. Pat. Nos. 6,916,661; 6,939,720; 7,141,431; 7,445,844; 7,465,540; 8,038,734; and 8,088,629, all of which are incorporated herein by reference in their entirety.

In some embodiments, the immunoassay used to detect an antibody specific for an *M. tb* antigen according to the present invention is an enzyme-linked immunosorbent assay (ELISA) or more generically termed an enzyme immunoassay (EIA). In such assays, a detectable label bound to either an antibody-binding or antigen-binding reagent is an enzyme. When exposed to its substrate, this enzyme will react in such a manner as to produce a chemical moiety which can be detected, for example, by spectrophotometric, fluorometric or visual means. Enzymes which can be used to detectably label the reagents useful in the present invention include, but are not limited to, horseradish peroxidase, alkaline phosphatase, glucose oxidase, β-galactosidase, ribonuclease, urease, catalase, malate dehydrogenase, staphylococcal nuclease, asparaginase, delta-5-steroid isomerase, yeast alcohol dehydrogenase, α-glycerophosphate dehydrogenase, triose phosphate isomerase, glucose-6-phosphate dehydrogenase, glucoamylase and acetylcholinesterase. For descriptions of EIA procedures, see reference cited above or, additionally, Voller, A. et al., J. Clin. Pathol. 31:507-520 (1978); Butler, J. E., Meth. Enzymol. 73:482-523 (1981); Maggio, E. (ed.), Enzyme Immunoassay, CRC Press, Boca Raton, 1980.

In some embodiments, the immunoassay devices of the present invention permit the performance of relatively inexpensive, disposable, membrane-based assays for the visual identification of the presence (or absence) of an analyte in a liquid sample. Such devices are usually formatted as free-standing dipsticks (e.g., test strips) or as devices having some sort of housing. Typically, an immunoassay device of the present invention can be used with as little as about 200 µl of liquid sample, and detection of an analyte in the sample can (but need not) be complete within 2-5 minutes. In preferred embodiments, no ancillary instrumentation is required to perform such tests, and such devices easily can be used in clinics, laboratories, field locations, and the home even by inexperienced persons.

In some embodiments, the ELISA is an immunochromatographic "sandwich" assay. In general, sandwich immunochromatographic procedures call for mixing the sample that may contain the analyte to be assayed, for example, *M. tb* antibodies, with an antigenic composition or capture reagent as described above. A detector reagent is utilized which is mobile and typically is linked to a label or another signaling reagent, such as dyed latex, a colloidal metal sol, or a radioisotope. This mixture is then applied to a chromatographic medium containing a band or zone of immobilized antigenic compositions that serve as antigens for *M. tb* antibodies (i.e., the capture reagent). The chromatographic medium often is in the form of a strip that resembles a dipstick. When the complex of *M. tb* antibody and the detector reagent reaches the zone of the immobilized capture antibody on the chromatographic medium, binding occurs and the detector reagent complex is localized at the zone. This indicates the presence of the molecule to be assayed. This technique can be used to obtain quantitative or semi-quantitative results. Examples of sandwich immunoassays performed on test strips are described in U.S. Pat. Nos. 4,168,146 and 4,366,241, each of which is incorporated herein by reference.

In other embodiments, the ELISA is a solid phase immunoassay device that provides sensitive detection of analytes in biological fluid samples. Solid phase immunoassay devices incorporate a solid support to which one member of a ligand-receptor pair, usually an antibody, antigen, or hapten, is bound. Common early forms of solid supports were plates, tubes, or beads of polystyrene, which were known from the fields of radioimmunoassay and enzyme immunoassay. More recently, a number of porous materials such as nylon, nitrocellulose, cellulose acetate, glass fibers, and other porous polymers have been employed as solid supports. In other common forms of membrane-based immunoassays, as typified by some home pregnancy and ovulation detection kits, a test strip (or dipstick) is "dipped" into a sample suspected of containing the subject analyte. Enzyme-labeled detector reagent is then added, either simultaneously or after an incubation period. The device next is washed and then inserted into a second solution containing a substrate for the enzyme. The enzyme label, if present, interacts with the substrate, causing the formation of colored products, which either deposit as a precipitate onto the solid phase or produce a visible color change in the substrate solution. EP-A 0 125 118 describes such a sandwich type dipstick immunoassay. EP-A 0 282 192 describes a dipstick device for use in competition type assays.

In other embodiments, the assay device of the present invention is a flow through immunoassay device. Flow-through immunoassay devices involve a capture reagent (such as an immunogenic composition comprising at least of SEQ ID NOs:1-149) bound to a porous membrane or filter to which a liquid sample is added. As the liquid flows through the membrane, target analyte (such as an *M. tb* antibody) binds to the capture reagent. The addition of sample is followed by (or made concurrent with) addition of detector reagent (e.g., labeled second antibody). Alternatively, the detector reagent may be placed on the membrane in a manner that permits the detector to mix with the sample and thereby label the analyte. The visual detection of detector reagent provides an indication of the presence of target analyte in the sample. Representative flow-through immunoassay devices are described in U.S. Pat. Nos. 4,246,339; 4,277,560; 4,632,901; 4,812,293; 4,920,046; and 5,279,935; and U.S. Patent Application Publication Nos. 20030049857 and 20040241876, all of which are incorporated by reference in their entirety. In some embodiments, the assay device is a migration assay device. Such devices usually incorporate within them reagents that have been attached to colored labels, thereby permitting visible detection of the assay results without addition of further substances. See, for example, U.S. Pat. No. 4,770,853; PCT Publication No. WO 88/08534 and European Patent No. EP-A 0 299 428, all of which are incorporated by reference in their entirety.

In some embodiments, the assay device is lateral flow assay device. There are a number of commercially available lateral flow type tests and patents disclosing methods for the detection of analytes. See, e.g., U.S. Pat. Nos. 5,229,073; 5,591,645; 4,168,146; 4,366,241; 4,855,240; 4,861,711; 4,703,017; 5,451,504; 5,451,507; 5,798,273; 6,001,658; and 5,120,643; European Patent No. 0296724; WO 97/06439; and WO 98/36278, all of which are incorporated herein by reference.

The lateral flow assay devices of the present invention include a strip of absorbent or porous material (such as a microporous membrane), which, in some instances, can be made of different substances each joined to the other in zones, which may be abutted and/or overlapped. In some examples, the absorbent strip can be fixed on a supporting non-interactive material (such as nonwoven polyester), for example, to provide increased rigidity to the strip. Zones within each strip may differentially contain the specific binding partner(s) and/or other reagents required for the detection and/or quantification of the particular analyte being tested for, for example, *M. tb* antibodies. Thus these zones can be viewed as functional sectors or functional regions within the test device.

In some embodiments, a fluid sample (or a sample suspended in a fluid) is introduced to the strip at the proximal end of the strip, for instance by dipping or spotting. A sample is collected or obtained using methods well known to those skilled in the art. The sample containing the *M. tb* antibodies to be detected may be obtained from any biological source. Examples of biological sources include blood serum, blood plasma, urine, spinal fluid, saliva, fermentation fluid, lymph fluid, tissue culture fluid and ascites fluid of a human or animal. The sample may be diluted, purified, concentrated, filtered, dissolved, suspended or otherwise manipulated prior to immunoassay to optimize the immunoassay results. The fluid migrates distally through all the functional regions of the strip. The final distribution of the fluid in the individual functional regions depends on the adsorptive capacity and the dimensions of the materials used.

In some embodiments, porous solid supports, such as nitrocellulose, described hereinabove are preferably in the form of sheets or strips. The thickness of such sheets or strips may vary within wide limits, for example, from about 0.01 to 0.5 mm, from about 0.02 to 0.45 mm, from about 0.05 to 0.3 mm, from about 0.075 to 0.25 mm, from about 0.1 to 0.2 mm, or from about 0.11 to 0.15 mm. The pore size of such sheets or strips may similarly vary within wide limits, for example from about 0.025 to 15 microns, or more specifically from about 0.1 to 3 microns; however, pore size is not intended to be a limiting factor in selection of the solid support. The flow rate of a solid support, where applicable, can also vary within wide limits, for example from about 12.5 to 90 sec/cm (i.e., 50 to 300 sec/4 cm), about 22.5 to 62.5 sec/cm (i.e., 90 to 250 sec/4 cm), about 25 to 62.5 sec/cm (i.e., 100 to 250 sec/4 cm), about 37.5 to 62.5 sec/cm (i.e., 150 to 250 sec/4 cm), or about 50 to 62.5 sec/cm (i.e., 200 to 250 sec/4 cm). In specific embodiments of devices described herein, the flow rate is about 62.5 sec/cm (i.e., 250 sec/4 cm). In other specific embodiments of devices described herein, the flow rate is about 37.5 sec/cm (i.e., 150 sec/4 cm).

In some embodiments, the assay devices include a detector reagent. The detector reagent provides a means to detect the formation of a complex between an analyte (such as an *M. tb* antibody or antibodies) and a capture reagent (such as an antigenic composition as described above). A detector may be integrated into an immunoassay device (for example included in a conjugate pad, as described below), or may be applied to the device from an external source.

A detector may be a single reagent or a series of reagents that collectively serve the detection purpose. In some instances, a detector reagent is a labeled binding partner specific for the analyte. In other instances, a detector reagent collectively includes an unlabeled first binding partner specific for the analyte and a labeled second binding partner specific for the first binding partner and so forth. In each instance, a detector reagent specifically detects bound analyte of an analyte-capture reagent complex and, therefore, a detector reagent preferably does not substantially bind to or react with the capture reagent or other components localized in the analyte capture area. Such non-specific binding or reaction of a detector may provide a false positive result. Optionally, a detector reagent can specifically recognize a positive control molecule (such as a non-specific human IgG for a labeled Protein A detector, or a labeled Protein G detector, or a labeled anti-human Ab(Fc)) that is present in a secondary capture area.

The flow-through devices of the present invention comprise a capture reagent (e.g., antigenic composition as described above) immobilized on a solid support such as a microtiter plate or a membrane (such as, nitrocellulose, nylon, or PVDF). Characteristics of useful membrane have been previously described; however, it is useful to note that in a flow-through assay capillary rise is not a particularly important feature of a membrane as the sample moves vertically through the membrane rather than across it as in a lateral flow assay. In a simple representative format, the membrane of a flow-through device is placed in functional or physical contact with an absorbent layer (see, e.g., description of "absorbent pad" below), which acts as a reservoir to draw a fluid sample through the membrane. Optionally, following immobilization of a capture reagent, any remaining protein-binding sites on the membrane can be blocked (either before or concurrent with sample administration) to minimize nonspecific interactions.

In operation of a flow-through device, a fluid sample (such as a bodily fluid sample) is placed in contact with the membrane. Typically, a flow-through device also includes a sample application area (or reservoir) to receive and temporarily retain a fluid sample of a desired volume. The sample passes through the membrane matrix. In this process, an analyte in the sample (e.g., M. tb antibody or antibodies) can specifically bind to the immobilized capture reagent. Where detection of an analyte-capture reagent complex is desired, a detector reagent (e.g., labeled Protein A, labeled second antibody) can be added with the sample or a solution containing a detector reagent can be added subsequent to application of the sample. If an analyte is specifically bound by capture reagent, a visual representative attributable to the particular detector reagent can be observed on the surface of the membrane. Optional wash steps can be added at any time in the process, for instance, following application of the sample, and/or following application of a detector reagent.

A lateral flow device is an analytical device comprising a test strip, through which flows a test sample fluid that is suspected of containing an analyte of interest. The test fluid and any suspended analyte can flow along the strip to a detection zone in which the analyte (if present) interacts with a capture agent and a detection agent to indicate a presence, absence and/or quantity of the analyte. Many lateral flow devices are one-step lateral flow assays in which a biological fluid is placed in a sample area on a bibulous strip (though, non-bibulous materials can be used, and rendered bibulous, e.g., by applying a surfactant to the material), and allowed to migrate along the strip until the liquid comes into contact with a specific binding partner that interacts with an analyte in the liquid. Once the analyte interacts with the binding partner, a signal (such as a fluorescent or otherwise visible dye) indicates that the interaction has occurred. Multiple discrete binding partners can be placed on the strip (for example in parallel lines) to detect multiple analytes in the liquid. The test strips can also incorporate control indicators, which provide a signal that the test has adequately been performed, even if a positive signal indicating the presence (or absence) of an analyte is not seen on the strip.

The construction and design of lateral flow devices is described, for example, in Millipore Corporation, A Short Guide Developing Immunochromatographic Test Strips, 2nd Edition, pp. 1-40, 1999, available by request at (800) 645-5476; and Schleicher & Schuell, Easy to Work with Bio-Science, Products and Protocols 2003, pp. 73-98, 2003, available by request at Schleicher & Schuell BioScience, Inc., 10 Optical Avenue, Keene, N.H. 03431, (603) 352-3810; both of which are incorporated herein by reference. Lateral flow devices have a wide variety of physical formats. Any physical format that supports and/or houses the basic components of a lateral flow device in the proper function relationship is contemplated by this disclosure.

In some embodiments, lateral flow devices of the present invention comprise an elongated housing containing a bibulous lateral flow strip that extends substantially the entire length of housing. In some embodiments, the lateral flow strip is divided into a proximal sample application pad positioned below a sample introduction port, an intermediate test result membrane, and a distal absorbent pad. The flow strip is interrupted by a conjugate pad that contains labeled conjugate (such labeled second antibody). A flow path along the strip passes from the proximal pad, through conjugate pad, into a test result membrane, for eventual collection in absorbent pad. Selective binding agents (such as the antigenic compositions described above) are positioned on a proximal test line in the test result membrane. A control line is provided in the test result membrane slightly distal to the test line. A fluid sample containing an analyte of interest, such as M. tb antibody or antibodies, is applied to the sample pad through the sample introduction port. In some embodiments, the sample may be applied to the sample introduction port dropwise or by dipping the end of the device containing the sample introduction port into the sample. From the sample pad, the sample passes, for instance by capillary action, to the conjugate pad. In the conjugate pad, the analyte of interest may bind (or be bound by) a mobilized or mobilizable detector reagent. For example, an M. tb antibody may bind to a labeled (e.g., gold-conjugated) detector reagent (such as a second antibody contained in the conjugate pad. The analyte complexed with the detector reagent may subsequently flow to the test result membrane where the complex may further interact with a capture reagent, such as an antigenic composition as described above, which is immobilized at the proximal test line. The formation of the immunocomplex between M. tb antibody, labeled (e.g., gold-conjugated) detector reagent, and immobilized antigenic composition can be detected by the appearance of a visible line at the proximal test line, which results from the accumulation of the label (e.g., gold) in the localized region of the proximal test line. The control line may contain an immobilized, detector-reagent-specific binding partner, which can bind the detector reagent in the presence or absence of the analyte. Such binding at the control line indicates proper performance of the test, even in the absence of the analyte of interest.

The particular materials used in a particular lateral flow device will depend on a number of variables, including, for example, the analyte to be detected, the sample volume, the desired flow rate and others. In some embodiments, the sample pad receives the sample, and may serve to remove particulates from the sample. In some embodiments, the sample pad is cellulose. Sample pads may be treated with one or more release agents, such as buffers, salts, proteins, detergents, and surfactants. Such release agents may be useful, for example, to promote resolubilization of conjugate-pad constituents, and to block non-specific binding sites in other components of a lateral flow device, such as a nitrocellulose membrane. Representative release agents include, for example, trehalose or glucose (1%-5%), PVP or PVA (0.5%-2%), Tween 20 or Triton X-100 (0.1%-1%), casein (1%-2%), SDS (0.02%-5%), and PEG (0.02%-5%).

The conjugate pad holds a detector reagent. In some embodiments, a detector reagent may be applied externally, for example, from a developer bottle, in which case a lateral flow device need not contain a conjugate pad (see, for example, U.S. Pat. No. 4,740,468). Detector reagent(s) contained in a conjugate pad is typically released into solution upon application of the test sample. A conjugate pad may be treated with various substances to influence release of the detector reagent into solution. For example, the conjugate pad may be treated with PVA or PVP (0.5% to 2%) and/or Triton X-100 (0.5%). Other release agents include, without limitation, hydroxypropylmethyl cellulose, SDS, Brij and β-lactose.

The absorbent pad acts to increase the total volume of sample that enters the device. This increased volume can be useful, for example, to wash away unbound analyte from the membrane. Any of a variety of materials is useful to prepare an absorbent pad. In some device embodiments, an absorbent pad can be paper (i.e., cellulosic fibers). One of skill in the art may select a paper absorbent pad on the basis of, for example, its thickness, compressibility, manufacturability, and uniformity of bed volume. The volume uptake of an absorbent made may be adjusted by changing the dimensions (usually the length) of an absorbent pad.

A wide variety of detectable labels are useful with the assays described above in addition to the described enzymatic labels.

In another embodiment, the detectable label may be a gold or silver nanoparticle that can be enhanced with non-enzymatic silver deposition (SilverQuant™). Methods for detection with silver or gold nanoparticles are described in detail in U.S. Pat. No. 7,321,829, incorporated by reference herein its entirety, as well as in US PUBL. 20090253586, also incorporated herein by reference in its entirety.

In another embodiment, the detectable label may be a Proximity Ligation Assay (PLA) reagent[25]. Proximity ligation assay (PLA) is an approach for protein quantitation that can use two different binder molecules (proximity probes) to bind to a specific detection target (See for example Fredriksson, S. et al., Nat Biotechnol. 2002; 20(5): 473-77, Gullberg, M., et. al., Proc Natl Acad Sci USA. 2004; 101(22): 8420-24, Gullberg, M., et. al., Curr Opin Biotechnol. 2003; 14: 1-5, Pai, S., Ellington, A. D. and Levy, M., Nuc Acids Res. Oct. 19, 2005; 33(18): e162, Landegren, U. and Fredriksson, S., US Patent Application 20020064779, May 30, 2002, Fredriksson, S., US Patent Application 20050003361, all pof which are incorporated by reference herein in their entirety. Typical binders include polyclonal or monoclonal antibody pairs. Each binder molecule can be conjugated to a specific oligonucleotide. One binder's oligonucleotide can form the "left" side of a real-time PCR amplicon, while the other binder can form the "right" side. When the two binders find and attach to the same target, the left and right oligomers are brought into close proximity. With the addition of a connector oligonucleotide (splint) and ligase enzyme, the left and right oligomers can become ligated and thereby allow for the formation of a complete target for a real-time PCR. Further addition of Taqman reaction components followed by thermocycling generates real-time sequence detection data output.

In another embodiment, the detectable label may be a radiolabel, and the assay termed a radioimmunoassay (RIA), as is well known in the art. The radioisotope can be detected by a gamma counter, a scintillation counter or by autoradiography. Isotopes which are particularly useful for the purpose of the present invention are $^{125}I$, $^{131}I$, $^{35}S$, $^{3}H$ and $^{14}C$.

It is also possible to label the antigen or antibody reagents with a fluorophore. When the fluorescently labeled antibody is exposed to light of the proper wave length, its presence can then be detected due to fluorescence of the fluorophore. Among the most commonly used fluorophores are fluorescein isothiocyanate, rhodamine, phycoerythrin, phycocyanin, allophycocyanin, o-phthaldehyde, fluorescamine or fluorescence-emitting metals such as $^{152}Eu$ or other lanthanides. These metals are attached to antibodies using metal chelators.

The antigen or antibody reagents useful in the present invention also can be detectably labeled by coupling to a chemiluminescent compound. The presence of a chemiluminescent-tagged antibody or antigen is then determined by detecting the luminescence that arises during the course of a chemical reaction. Examples of useful chemiluminescent labeling compounds are luminol, isoluminol, theromatic acridinium ester, imidazole, acridinium salt and oxalate ester. Likewise, a bioluminescent compound such as a bioluminescent protein may be used to label the antigen or antibody reagent useful in the present invention. Binding is measured by detecting the luminescence. Useful bioluminescent compounds include luciferin, luciferase and aequorin.

Detection of the detectably labeled reagent according to the present invention may be accomplished by a scintillation counter, for example, if the detectable label is a radioactive gamma emitter, or by a fluorometer, for example, if the label is a fluorophore. In the case of an enzyme label, the detection is accomplished by colorimetry to measure the colored product produced by conversion of a chromogenic substrate by the enzyme. Detection may also be accomplished by visual comparison of the colored product of the enzymatic reaction in comparison with appropriate standards or controls.

In some embodiments, the one or more of the peptides or conjugates described above (alone or in combination) are used as an antigen stimulation mixture for cell based assays including, but not limited to, cytokine release assays (particularly interferon gamma release and interleukin 12) as measured by ELISA, Elispot, or bead based methods. In other embodiments, the peptides or conjugates described above (alone or in combination) are used in T-cell capture assays. In still other embodiments, the peptides or conjugates described above (alone or in combination) are used as an antigenic substitute for tuberculin in the tuberculin skin test (TST).

In some embodiments, the present invention provides kits for use in detecting *M. tb* antibodies in a sample (such as, a biological sample). Such kits can be used, for example, to determine whether an animal has been exposed to *M. tb* or has an *M. tb* infection. Certain embodiments of the disclosed kits are generally portable and provide a simple, rapid, and/or cost-effective way to determine *M. tb* infection without the need for specialized laboratory facilities, such as in a point-of-care facility.

In some embodiments, the kits of the present invention include one or more immunoassay devices (and/or antigen-coated microtiter plates) as disclosed herein and a carrier means, such as a box, a bag, a satchel, plastic carton (such as molded plastic or other clear packaging), wrapper (such as, a sealed or sealable plastic, paper, or metallic wrapper), or other container. In some examples, kit components will be enclosed in a single packaging unit, such as a box or other container, which packaging unit may have compartments into which one or more components of the kit can be placed. In other examples, a kit includes one or more containers, for instance vials, tubes, and the like that can retain, for example, one or more biological samples to be tested, positive and/or negative control samples or solutions (such as, a positive control serum containing *M. tb* antibodies), diluents (such as, phosphate buffers, or saline buffers), detector reagents (e.g., for external application to a kit device), substrate reagents for visualization of detector reagent enzymes (such as, 5-bromo-4-chloro-3-indolyl phosphate, nitroblue tetrazolium in dimethyl formamide), and/or wash solutions (such as, Tris buffers, saline buffer, or distilled water).

Other kit embodiments include syringes, finger-prick devices, alcohol swabs, gauze squares, cotton balls, bandages, latex gloves, incubation trays with variable numbers of troughs, adhesive plate sealers, data reporting sheets, which may be useful for handling, collecting and/or processing a biological sample. Kits may also optionally contain implements useful for introducing samples into a sample chamber of an immunoassay device, including, for example, droppers, Dispo-pipettes, capillary tubes, rubber bulbs (e.g., for capillary tubes), and the like. Still other kit embodiments may include disposal means for discarding a used immunoassay device and/or other items used with the device (such as patient samples, etc.). Such disposal means can include, without limitation, containers that are capable of containing leakage from discarded materials, such as plastic, metal or other impermeable bags, boxes or containers.

In some embodiments, a kit of the present invention will include instructions for the use of an immunoassay device or antigen-coated plate. The instructions may provide direction on how to apply sample to the test device or plate, the amount of time necessary or advisable to wait for results to develop, and details on how to read and interpret the results of the test. Such instructions may also include standards, such as standard tables, graphs, or pictures for comparison of the results of a test. These standards may optionally include the information necessary to quantify analyte using the test device, such as a standard curve relating intensity of signal or number of signal lines to an amount of analyte therefore present in the sample.

In some embodiments, the present invention provides a vaccine comprising one or more of the peptides described above (i.e. SEQ ID NOs.:1-149). As used herein, the term "vaccine" refers to any combination of peptides or a single peptide formulation. There are various reasons why one might wish to administer a vaccine of a combination of the peptides of the present invention rather than a single peptide. Depending on the particular peptide that one uses, a vaccine might have superior characteristics as far as clinical efficacy, solubility, absorption, stability, toxicity and patient acceptability are concerned. It should be readily apparent to one of ordinary skill in the art how one can formulate a vaccine of any of a number of combinations of peptides of the present invention. There are many strategies for doing so, any one of which may be implemented by routine experimentation.

The peptides of the present invention may be administered as a single agent therapy or in addition to an established therapy, such as inoculation with live, attenuated, or killed virus, or any other therapy known in the art to treat the target disease or epitope-sensitive condition.

The appropriate dosage of the peptides of the invention may depend on a variety of factors. Such factors may include, but are in no way limited to, a patient's physical characteristics (e.g., age, weight, sex), whether the compound is being used as single agent or adjuvant therapy, the type of MHC restriction of the patient, the progression (i.e., pathological state) of the infection or other epitope-sensitive condition, and other factors that may be recognized by one skilled in the art. In general, an epitope or combination of epitopes may be administered to a patient in an amount of from about 50 micrograms to about 5 mg; dosage in an amount of from about 50 micrograms to about 500 micrograms is especially preferred.

In some embodiments, the peptides are expressed on bacteria, such as *lactococcus* and *lactobacillus*, or expressed on virus or virus-like particles for use as vaccines. In some embodiments, the peptides are incorporated into other carriers as are known in the art. For example, in some embodiments, the polypeptides comprising one or more epitopes are conjugated or otherwise attached to a carrier protein. Suitable carrier proteins include, but are not limited to keyhole limpet hemocyanin, bovine serum albumin, ovalbumin, and thyroglobulin. In yet other embodiments the polypeptide may be fused to an Fc region of an immunoglobulin for delivery to a mucosal site bearing corresponding receptors.

One may administer a vaccine of the present invention by any suitable method, which may include, but is not limited to, systemic injections (e.g., subcutaneous injection, intradermal injection, intramuscular injection, intravenous infusion) mucosal administrations (e.g., nasal, ocular, oral, vaginal and anal formulations), topical administration (e.g., patch delivery), or by any other pharmacologically appropriate technique. Vaccination protocols using a spray, drop, aerosol, gel or sweet formulation are particularly attractive and may be also used. The vaccine may be administered for delivery at a particular time interval, or may be suitable for a single administration.

Vaccines of the invention may be prepared by combining at least one peptide with a pharmaceutically acceptable liquid carrier, a finely divided solid carrier, or both. As used herein, "pharmaceutically acceptable carrier" refers to a carrier that is compatible with the other ingredients of the formulation and is not toxic to the subjects to whom it is administered. Suitable such carriers may include, for example, water, alcohols, natural or hardened oils and waxes, calcium and sodium carbonates, calcium phosphate, kaolin, talc, lactose, combinations thereof and any other suitable carrier as will be recognized by one of skill in the art. In a most preferred embodiment, the carrier is present in an amount of from about 10 uL (micro-Liter) to about 100 uL.

In some embodiments, the vaccine composition includes an adjuvant. Examples of adjuvants include, but are not limited to, mineral salts (e.g., aluminum hydroxide and aluminum or calcium phosphate gels); oil emulsions and surfactant based formulations (e.g., MF59 (microfluidized detergent stabilized oil-in-water emulsion), QS21 (purified saponin), Ribi Adjuvant Systems, AS02 [SBAS2] (oil-in-water emulsion+MPL+QS-21), Montanide ISA-51 and ISA-720 (stabilized water-in-oil emulsion); particulate adjuvants (e.g., virosomes (unilamellar liposomal vehicles incorporating influenza haemagglutinin), AS04 ([SBAS4] Al salt with MPL), ISCOMS (structured complex of saponins and lipids), polylactide co-glycolide (PLG); microbial derivatives (natural and synthetic), e.g., monophosphoryl lipid A (MPL), Detox (MPL+M. *Phlei* cell wall skeleton), AGP [RC-529] (synthetic acylated monosaccharide), DC_Chol (lipoidal immunostimulators able to self organize into liposomes), OM-174 (lipid A derivative), CpG motifs (synthetic oligonucleotides containing immunostimulatory CpG motifs), modified LT and CT (genetically modified bacterial toxins to provide non-toxic adjuvant effects); endogenous human immunomodulators (e.g., hGM-CSF or hIL-12 (cytokines that can be administered either as protein or plasmid encoded), Immudaptin (C3d tandem array); and inert vehicles, such as gold particles. In various embodiments, vaccines according to the invention may be combined with one or more additional components that are typical of pharmaceutical formulations such as vaccines, and can be identified and incorporated into the compositions of the present invention by routine experimentation. Such additional components may include, but are in no way limited to, excipients such as the following: preservatives, such as ethyl-p-hydroxybenzoate; suspending agents such as methyl cellulose, tragacanth, and sodium alginate; wetting agents such as lecithin, polyoxyethylene stearate, and polyoxyethylene sorbitan mono-oleate; granulating and disintegrating agents such as starch and alginic acid; binding agents such as starch, gelatin, and acacia; lubricating agents such as magnesium stearate, stearic acid, and talc; flavoring and coloring agents; and any other excipient conventionally added to pharmaceutical formulations.

Further, in various embodiments, vaccines according to the invention may be combined with one or more of the group consisting of a vehicle, an additive, a pharmaceutical adjunct, a therapeutic compound or agent useful in the treatment of the desired disease, and combinations thereof.

EXAMPLES

Example 1

Material and Methods
Peptides

A partial proteome mapping peptide array of 6912 peptides 15 amino acids in length with a 12 amino acid overlap (product RT-HD-TUB) for the reference strain *Mycobacterium tuberculosis* H37Rv (JPT Peptide Technologies, GmbH, Berlin, Germany) was used to perform preliminary studies. A refined set of 1075 peptides were designed for proteins of interest from these experiments, covering 246 proteins, with 15 amino acid length with a 3 amino acid overlap.

Array Preparation

Arrays were manufactured with peptides synthesized in the manner described in Nahtman et al[27]. Briefly, 1 mM solution of each peptide was printed on epoxy functionalized glass slides (Corning Epoxy #440042) using a contact array printer (JPT Peptide). Arrays were printed such that each peptide was printed in triplicate. For the refined set of 1075 peptides, arrays were printed with 4 subarrays per slide, with triplicate spots. Human IgG was printed as internal controls for the assay, and orientation for the data analysis.

Serum Samples

Preliminary experiments were performed with samples generously donated by the Pathogen Detection Laboratory at the California National Primate Center (University of California-Davis, Davis, Calif.). Six serum samples were used for the preliminary studies, including 4 time points during a course of an intentional experimental infection, and serum from 2 known test positive macaques.

Samples for assays performed on the refined arrays were generously donated by the Oregon National Primate Research Center (Oregon Health and Science University, Beaverton, Oreg.). Sera from twelve animals quarantined and necropsied following an outbreak of *M. tb* in the colony were compared with sera from previous blood collections, 1-2 years prior to the outbreak. In addition to pre-infection sera, 4 test negative samples from the same colony were also run on the refined arrays to establish an average "non-infected" immune profile. Additionally, 56 test negative samples from the Wisconsin National Primate Center (gift of Dr. Jonah Sacha) and the Caribbean National Primate Center (gift of Dr. Carlos Sariol) were also included in the negative serum set. Table 1 shows the individual serum samples, their source, and previous test results for tuberculin skin test (TST) and other confirmatory testing. Sera were stored at −80° C. until use.

TABLE 1

| Sample ID | Source | Sample Type | Disease State | TST Test |
|---|---|---|---|---|
| 17846 | WNPRC | Normal | Naïve | Negative |
| 17847 | WNPRC | Normal | Naïve | Negative |
| 17848 | WNPRC | Normal | Naïve | Negative |
| 17849 | WNPRC | Normal | Naïve | Negative |
| 17850 | WNPRC | Normal | Naïve | Negative |
| 17851 | WNPRC | Normal | Naïve | Negative |
| 17852 | WNPRC | Normal | Naïve | Negative |
| 17853 | WNPRC | Normal | Naïve | Negative |
| 17854 | WNPRC | Normal | Naïve | Negative |
| 17855 | WNPRC | Normal | Naïve | Negative |
| 17856 | WNPRC | Normal | Naïve | Negative |
| 17857 | WNPRC | Normal | Naïve | Negative |
| 17858 | WNPRC | Normal | Naïve | Negative |
| 17859 | WNPRC | Normal | Naïve | Negative |
| 17860 | WNPRC | Normal | Naïve | Negative |
| 17861 | WNPRC | Normal | Naïve | Negative |
| 17862 | WNPRC | Normal | Naïve | Negative |
| 17863 | WNPRC | Normal | Naïve | Negative |
| 17864 | WNPRC | Normal | Naïve | Negative |
| 17865 | WNPRC | Normal | Naïve | Negative |
| 17866 | WNPRC | Normal | Naïve | Negative |
| 17867 | WNPRC | Normal | Naïve | Negative |
| 17868 | WNPRC | Normal | Naïve | Negative |
| 17869 | WNPRC | Normal | Naïve | Negative |
| 20758 | ONPRC | Disease | Post | Positive |
| 20284 | ONPRC | Disease | Post | Positive |
| 22319 | ONPRC | Disease | Post | Positive |
| 28642 | ONPRC | Disease | Post | Positive |
| 28643 | ONPRC | Disease | Post | Positive |
| 28655 | ONPRC | Disease | Post | Positive |
| 28667 | ONPRC | Disease | Post | Positive |
| 28674 | ONPRC | Disease | Post | Positive |
| 28676 | ONPRC | Disease | Post | Positive |
| 28677 | ONPRC | Disease | Post | Positive |
| 29417 | ONPRC | Disease | Post | Positive |
| 20758 | ONPRC | Normal | Pre | Negative |
| 20284 | ONPRC | Normal | Pre | Negative |
| 22319 | ONPRC | Normal | Pre | Negative |
| 28642 | ONPRC | Normal | Pre | Negative |
| 28643 | ONPRC | Normal | Pre | Negative |
| 28655 | ONPRC | Normal | Pre | Negative |

TABLE 1-continued

| Sample ID | Source | Sample Type | Disease State | TST Test |
|---|---|---|---|---|
| 28667 | ONPRC | Normal | Pre | Negative |
| 28674 | ONPRC | Normal | Pre | Negative |
| 28676 | ONPRC | Normal | Pre | Negative |
| 28677 | ONPRC | Normal | Pre | Negative |
| 29417 | ONPRC | Normal | Pre | Negative |
| 27790 | ONPRC | Normal | Naïve | Negative |
| 26023 | ONPRC | Normal | Naïve | Negative |
| 22819 | ONPRC | Normal | Naïve | Negative |
| 23351 | ONPRC | Normal | Naïve | Negative |
| 18171 | CaNPRC | Normal | Naïve | Negative |
| 18172 | CaNPRC | Normal | Naïve | Negative |
| 18173 | CaNPRC | Normal | Naïve | Negative |
| 18174 | CaNPRC | Normal | Naïve | Negative |
| 18175 | CaNPRC | Normal | Naïve | Negative |
| 18176 | CaNPRC | Normal | Naïve | Negative |
| 18177 | CaNPRC | Normal | Naïve | Negative |
| 18178 | CaNPRC | Normal | Naïve | Negative |
| 18179 | CaNPRC | Normal | Naïve | Negative |
| 18180 | CaNPRC | Normal | Naïve | Negative |
| 18181 | CaNPRC | Normal | Naïve | Negative |
| 18182 | CaNPRC | Normal | Naïve | Negative |
| 18183 | CaNPRC | Normal | Naïve | Negative |
| 18184 | CaNPRC | Normal | Naïve | Negative |
| 18185 | CaNPRC | Normal | Naïve | Negative |
| 18186 | CaNPRC | Normal | Naïve | Negative |
| 18187 | CaNPRC | Normal | Naïve | Negative |
| 18188 | CaNPRC | Normal | Naïve | Negative |
| 18189 | CaNPRC | Normal | Naïve | Negative |
| 18190 | CaNPRC | Normal | Naïve | Negative |
| 18191 | CaNPRC | Normal | Naïve | Negative |
| 18192 | CaNPRC | Normal | Naïve | Negative |
| 18193 | CaNPRC | Normal | Naïve | Negative |
| 18194 | CaNPRC | Normal | Naïve | Negative |
| 18195 | CaNPRC | Normal | Naïve | Negative |
| 18196 | CaNPRC | Normal | Naïve | Negative |
| 18197 | CaNPRC | Normal | Naïve | Negative |
| 18198 | CaNPRC | Normal | Naïve | Negative |
| 18199 | CaNPRC | Normal | Naïve | Negative |
| 18200 | CaNPRC | Normal | Naïve | Negative |
| 18201 | CaNPRC | Normal | Naïve | Negative |
| 18202 | CaNPRC | Normal | Naïve | Negative |

| Key | |
|---|---|
| Naïve | Normal, uninfected animal |
| Pre | Normal sample from animal that later was diagnosed with TB |
| Post | Disease sample from animal diagnosed with TB |
| ONPRC | Oregon National Primate Center |
| WNPRC | Wisconsin National Primate Center |
| CaNRPC | Caribbean National Primate Center |

Sample Processing

A reusable frame and gasket system (Intuitive Biosciences, Madison, Wis.) for incubation was applied to the peptide microarrays. Serum was diluted 1:100 in Dilution Buffer (Intuitive Biosciences), and incubated in one well of the array. Detection of bound IgG from the serum samples was performed using the CSA: Simian Detection kit (Intuitive Biosciences). Briefly, diluted serum was incubated for 1 hr at room temperature. Each well was washed 5 times, followed by addition of a biotinylated anti-simian IgG antibody diluted 1:10,000, and incubated for 1 hour at room temperature. After 5 repeat washes, 1 mL of gold conjugated anti-biotin was incubated for 45 minutes at room temperature. After 5 wash steps, slides were rinsed with 1 mL of water and immune complexes visualized by addition of SilverQuant® reagents (Intuitive Biosciences). After 3 minutes incubation in dark, slides were quickly washed with water and dried.

Data Acquisition

The peptide microarray slides were scanned with the AthenaQuant System from Intuitive Biosciences. Saved images were analyzed with AthenaQuant® software from Intuitive Biosciences, and background subtracted data exported in Excel files. Relative Intensity Units (RIU) were calculated by AthenaQuant and reported for each peptide feature on the microarray.

Statistical Analysis

Preliminary studies used RIU data from the mean of triplicate spots for each sample to calculate a fold over normal value.

The majority of the data management and analysis steps were accomplished with the Golden Helix SNP & Variation Suite (SVS) software version 7.5 (Golden Helix, Boseman, Mont.). Data was normalized by two methods: quantile normalization and Principal Components Analysis. Comparisons of infected and normal samples were conducted using two statistical tests: a Two-Sample T-Test and a Mann-Whitney (MW) Rank Sum Test. Two t-tests and two MW tests were performed. Each test was performed for the comparison of the matched pair (pre infection vs post infection) data and the comparison of the 12 TB-positive samples to the 60 naive samples. The matched-pair tests were performed only in quantile-normalized data, while the 12 positive vs 60 naive tests were performed in the PCA-corrected data. The resulting p-values for each comparison were reported in Excel, and a sum of the p-values for the four tests were calculated and used to sort the peptides in order of significance.

Results

Samples from the Oregon National Primate Center (ONPRC) were acquired following a series of positive TST during routine screening. One animal presented a positive TST, resulting in the immediate quarantine of that animal and the other housed in the same room, a total of twelve animals. Several tests were performed in parallel with repeated TST on the quarantined animals. Of the 12 animals, 7 tested positive by TST performed at the ONPRC. A PrimaTB STAT-Pak, referred to as Lateral Flow in Table 2, was performed according to the manufacturer's instructions by the ONPRC. Whole blood samples were collected from these animals and sent to the Pathogen Detection Laboratory at UC-Davis (PDL), where the Primagam assay for measuring IFN-γ release was performed alongside an ESAT-6 ELISA for detection of ESAT-6 specific antibodies. At least 7 animals tested positive by these methods, and the animals were euthanized and post-mortem testing performed. *Mycobacterium* culture was performed from lung samples by the National Veterinary Services Laboratories (Ames, Iowa) and found 8 samples culture positive. Additionally, PCR testing for detection of Mycobacteria from the samples was performed by the Washington Animal Disease Diagnostic Lab (WADDL) but only found a few positive samples. Lastly, gross pathology of lungs was performed during necropsy of the animals and lesions were found in ten of the twelve animals. Serum samples collected from these twelve animals during quarantine were received along with serum samples from blood draws at least 2 years prior to the outbreak, when the animals had negative TST. These pre-infection and post-infection samples were used in addition to the other naïve samples listed in Table 1 to perform antibody detection assays using the refined TB peptide microarrays. Statistical analysis of the 12 positive sera compared to the 60 naïve sera was performed, and a set of 5 peptides were chosen as epitopes to distinguish between naïve and positive samples. Using these 5 peptides as classifiers, the results for the "post" or infected samples for the 12 animals was divided by the "pre" or non-infected sample. The log 2 ratio of the fold over naïve was calculated for the 12 animals, and the sum of these 5 ratios calculated. The sum of the log 2 ratios is shown in Table 2. Importantly, animal 28647 that was negative by every method of testing showed no difference in the "pre" and "post" measurements, while the remaining 11 samples scored greater than 6 (at least a 2-fold increase in the "pre" to "post" measurement for several of the 5 classifier peptides).

format. From these experiments, 4 peptide-BSA conjugates were mixed, each at 25 µg/ml in Array Print Buffer (IBI) and arrayed onto Protein Microarray Slides along with other viral Ag from the CSA: Simian Basic (IBI).

Serum Samples—

The initial Ab screen was performed in 2 separate experiments using serum samples from rhesus macaques donated by the Pathogen Detection Laboratory at the California NPRC (CNPRC; University of California-Davis). A total of 4 positive serum samples were analyzed; 3 samples from an

TABLE 2

TB analysis summary for NHPs from ONPRC. Twelve NHPs were assessed for TB disease using TST, PRIMAGRAM, Lateral Flow (PrimaTB SAT-Pak), ESAT-6 ELISA, tubercule lesions, M. tb culture, and PCR analysis for M. tb gene sequences. Results from this work are shown as Intuitive Bio. Analysis was determined by the sum of the fold-change (FC) of specific peptides compared to negative controls (see text). Analysis results: positive (+), weak positive (+/−), negative (−), and not analyzed (N/A).

| | | Animal | | | | | | | | | | | |
|---|---|---|---|---|---|---|---|---|---|---|---|---|---|
| Test Type | | 1 | 2 | 3 | 4 | 5 | 6 | 7 | 8 | 9 | 10 | 11 | 12 |
| Intuitive Bio | Sum FC-pre | − | − | − | − | − | +/− | − | − | − | − | − | − |
| | Sum FC-post | + | − | +/− | + | + | +/− | + | + | +/− | + | + | + |
| Antemortem | TST | − | − | + | − | + | − | − | + | + | + | + | + |
| | Primagam | − | − | + | +/− | + | − | + | + | − | + | − | + |
| | Lat Flow | − | − | − | + | + | − | − | − | + | − | + | − |
| | ESAT-6 | +/− | +/− | − | − | +/− | − | − | − | +/− | − | − | +/− |
| Postmortem | Lesions | +/− | − | + | + | + | − | +/− | + | +/− | + | + | + |
| | Culture | + | N/A | + | + | + | − | + | + | + | + | N/A | − |
| | PCR | − | N/A | − | − | − | N/A | − | + | − | − | − | − |

Example 2

This example demonstrates the use of peptide microarrays to discover novel peptide biomarkers. Briefly, JPT microarrays were incubated with diluted serum from M. tb infected and normal NHPs and absorbed Ab detected with biotinylated anti-simian IgG. Anti-biotin IgG-gold conjugate and SilverQuant® silver deposition technology detected the biotin on the microarray slides. Slides with silver spots were imaged using the AthenaQuant® System, scanned, and analyzed to quantify the silver spots. Relative spot intensities from infected animals were compared to normal samples to identify peptides that best differentiated infected from normal. These peptides were synthesized, conjugated to BSA, and the discrimination verified in an Ag microarray using additional serum samples and the same detection technology.

Methods

Screening Peptide Microarrays—

The initial Ab screen employed a selected segment of the M. tb proteome, determined from the sequenced genome of the reference strain M. tb H37Rv. The peptide microarray consisted of 6,912 15-aa peptides, each with a 12-aa overlap. Based on the results, JPT constructed a custom peptide micro-array with 1,075 15-aa peptides, each with a 3-aa overlap, that encompass 246 different M. tb proteins (secondary screen). The initial screen contained 1 array/slide (i.e., for 1 sample); the custom array had 4 sub-arrays per slide.

Verification Peptide Microarray—

Based on the initial and secondary screening results, 20 peptides were synthesized with a carboxyl terminal cysteine and conjugated to BSA through a NHS-maleimide linker (Pierce Bio-technologies) and arrayed, both individually and mixed, at optimal concentrations and printing formulations onto Protein Microarray Slides (IBI) in a 24 sub-array experimental infection time-course experiment [2, 4, and 20 weeks post-infection (WPI)] and 1 sample from a macaque that tested positive by the TST, PCR, and culture (natural infection). The pre-infection sample was used as the negative control serum.

The secondary screen using the custom array was performed using samples donated by the Pathogen Detection Laboratory at CNPRC, the Oregon NPRC (ONPRC; Oregon Health and Science University, Beaverton, Oreg.), and Tulane NRPC (TNPRC; Tulane University). Positive serum samples from the ONPRC were derived from 12 animals that were initially quarantined, then euthanized and necropsied following an M. tb outbreak (natural infection) in a colony. The negative control sera from the same animals were from stored collections. Positive and negative (pre-infection) samples from TNPRC were drawn from an experimental infection time-course experiment with 5-6 points from 6 animals. In addition, 56 negative samples from the Wisconsin NPRC and the Caribbean NPRC were also analyzed in the secondary screen.

Screening Microarray Assay Method—

For the initial screen, the peptide microarray slides were assayed using the CSA: Simian Detection kit (Prod. No. 12-1006, Intuitive Biosciences) protocol. Briefly, Abs in diluted serum were permitted to bind to peptide Ags and were detected with a combination of biotinylated anti-simian IgG Ab and anti-biotin IgG-gold conjugate. Ab-gold complexes were visualized by adding SilverQuant® Reagents, the slides quickly washed with water and dried. The slides were imaged with the AthenaQuant System by Intuitive Biosciences, and scanned. Silver spots in the images were identified, quantified, and the background subtracted using AthenaQuant® software (Intuitive Biosciences). Quantified spot intensities were reported as relative intensity units (RIU) in Excel and matched to the appropriate peptide spot using a GAL (GenePix Array List) file from JPT (except for the verification assays).

Results

For the primary screening assay, we calculated the average RIU of triplicate spots for each peptide for each sample then divided this average by the average of the negative control sample for the same peptide. For each peptide, we calculated the sum of the fold change over the negative control ratio by adding the individual ratios of 2, 4, and 20 WPI with the natural infection sample to a Sum Fold Change (data not shown). We selected the top 756 peptides for further evaluation and inclusion on the secondary screening arrays.

The entire collection of available serum samples was assayed using the secondary screen peptide microarray. Heilman Consulting (Madison, Wis.) used quantile normalization and principal components analysis (PCA) to analyze 88 positive and 68 negative samples from ONPRC, CNPRC, and TNPRC. Infected and normal samples were compared using a Two-Sample T-Test and a Mann-Whitney (MW) Rank Sum Test. The 20 peptides with the highest rank are summarized in Table 3. Some peptides originate from well-known antigenic proteins, such as ESAT-6, while others are derived from proteins with unknown function and previously not known for immunogenicity in NHPs.

TABLE 3

Top 20 peptides. Using Two-Sample T-Test and a Mann-Whitney Rank Sum Test, peptides were assessed for discrimination of *M. tb* positive serum samples compared to negative samples.

| Peptide | Gene name | Protein Name |
|---|---|---|
| 1 | Rv0104 | conserved hypothetical protein |
| 2 | Rv2873 | cell surface lipoprotein MPT83 |
| 3 | Rv1037c, Rv1198, Rv3619c | putative ESAT-6 like protein |
| 4 | Rv2497c | putative alpha-keto acid dehydrogenase |
| 5 | Rv0918 | conserved hypothetical protein |
| 6 | Rv3875 | ESAT-6 |
| 7 | Rv3286c | sigF, sigma factor F |
| 8 | Rv1509 | conserved hypothetical protein |
| 9 | Rv0099 | possible fatty-acid-CoA synthetase |
| 10 | Rv0040c | 28 kDa antigen |
| 11 | Rv0019 | conserved hypothetical protein |
| 12 | Rv1926c | MPT63 |
| 13 | Rv3879c | espK |
| 14 | Rv3871 | ESX conserved, unknown function |
| 15 | Rv3875 | ESAT-6 |
| 16 | Rv0085 | putative hydrogenase |
| 17 | Rv1009 | putative resuscitation promoting factor |
| 18 | Rv2006 | putative trehalose-6-phosphate phosphatase |
| 19 | Rv0050 | putative ponA1, penicillin binding protein |
| 20 | Rv3874 | CFP-10 |

The samples acquired from the ONPRC had positive TST results during routine screening at the facility [personal communication, K. Andrews]. After one animal presented a positive TST, it was immediately quarantined along with the NHPs that were housed in the same enclosure—a total of 12 animals. Additional tests were performed in parallel on the quarantined animals. Of the 12 animals, 7 tested positive by TST (performed at the ONPRC). All 12 were then tested with a PrimaTB STAT-Pak lateral flow device (Chembio Diagnostic Systems), an IFGA (PRIMAGAM), and an ESAT-6 ELISA. Each animal was euthanized and a necropsy performed. *M. tb* culture was performed at National Veterinary Services Laboratories (Ames, Iowa) and PCR analysis at Washington Animal Disease Diagnostic Lab (WADDL). Finally, gross pathology of lungs was performed during necropsy to identify lesions indicative of tuberculosis. Table 2 above shows the results of the analyses and demonstrates the inability of current assays to conclusively identify a true tuberculosis infection as indicated by the necropsy results.

Serum samples from the same 12 NHPs were assayed using the secondary screen peptide microarray. The fold change (FC) increase in signal intensity for each peptide was calculated by dividing the RIU for the TB-infected sample by the mean of the 40 negative samples (pre-infection plus TST negatives). The sum of the FC for 20 individual peptides was calculated for each animal and shown in Table 2 as negative (<30), weak positive (30-45), and positive (>45). Using these qualifications, our assay results showed 11 of 12 animals had Abs specific to these 20 peptides.

Samples from experimentally TB-infected animals at TNPRC were run on IBI's verification peptide microarrays to determine each peptide's utility at identifying positive samples. Using 141 negatives and 35 positives (experimental and natural infections), a receiver operating characteristic (ROC) analysis was performed for each peptide (data not shown). Peptides 4, 6, 15, and 20 provided the best sensitivity and specificity, but no single peptide had >90% sensitivity. To improve this sensitivity, we pooled equal volumes of the 4 peptides (Mix A) to create an Ag mix that detected all positive samples (FIG. 1). For example, Sample CA75 was detected by Peptide 20 alone and Sample HI36 was detected by Peptide 15 alone. Notably, only 4 out of 20 peptides could discriminate between positive and negative serum samples. The Mix A formulation was optimized to reduce background signal (data not shown), arrayed, and used to screen 141 negative and 35 positive serum samples. An ROC analysis was performed and using a cutoff value of 7364 RIU, the calculated sensitivity was 97.1% and specificity was 87.2% (FIG. 2).

Example 3

This example demonstrates that not all ESAT-6 spanning peptides are useful to identify TB-positive animals. As can be seen in the following table, the first two peptides from the N—C terminus of ESAT-6 are not useful in distinguishing between TB positive and negative groups. This was taken from the second round of screening data. Peptides were selected that had a high p-value AND Mann-Whitney rank. The peptides not bolded were not used any further in the development process because they were not statistically relevant (no change between TB and negative groups) and had a low fold change rank. FC rank measured the magnitude of the response.

| Order | Probe ID | P-value (T-test) | P-value rank | MW Rank | FC rank |
|---|---|---|---|---|---|
| 1 | MTEQQWNFAGIEAAA | 0.019702746 | 239 | 304 | 44 |
| 2 | AAASAIQGNVTSIHS | 0.029676213 | 275 | 104 | 263 |

-continued

| Order | Probe ID | P-value (T-test) | P-value rank | MW Rank | FC rank |
|---|---|---|---|---|---|
| 3 | IHSLLDEGKQSLTKL | 5.92E-06 | 4 | 36 | 47 |
| 4 | TKLAAAWGGSGSEAY | 5.04E-06 | 3 | 1 | 3 |
| 5 | EAYQGVQQKWDATAT | 1.04E-07 | 2 | 4 | 1 |
| 6 | ELNNALQNLARTISE | 3.64E-05 | 9 | 677 | 20 |
| 8 | QAMASTEGNVTGMFA | 0.079415726 | 409 | 687 | 320 |

Example 4

Using a mix of peptides 6, 15, 17, and 20 on the CSA: Simian array platform, 6 of 12 positive samples were correctly identified. See FIG. 3. Looking at signal for individual peptides, early and active infection may be better identified by examining the RIU for Peptides 3 and 9, in addition to 6, 15, and 20. For latently infected animals, Peptides 2, 3, 15, 19, and 20 are seroreactive and may better identify latently infected animals.

REFERENCES

1. Lau, D. T., J. M. Fuller, and P. E. Sumner, *Tuberculosis in a pig-tailed macaque.* J Am Vet Med Assoc, 1972. 161(6): p. 696-9.
2. Bushmitz, M., et al., *Guidelines for the prevention and control of tuberculosis in non-human primates: recommendations of the European Primate Veterinary Association Working Group on Tuberculosis.* J Med Primatol, 2009. 38(1): p. 59-69.
3. Fourie, P. B. and M. W. Odendaal, *Mycobacterium tuberculosis in a closed colony of baboons (Papio ursinus).* Lab Anim, 1983. 17(2): p. 125-8.
4. Fox, J. G., et al., *Tuberculosis outbreak in rhesus monkeys immunosuppressed with antithymocyte globulin.* J Med Primatol, 1975. 7(5): p. 264-73.
5. Garcia, M. A., et al., *Outbreak of Mycobacterium bovis in a conditioned colony of rhesus (Macaca mulatta) and cynomolgus (Macaca fascicularis) macaques.* Comp Med, 2004. 54(5): p. 578-84.
6. Mayhall, C. G., V. A. Lamb, and P. H. Coleman, *Infection in rhesus (Macaca mulatta) and squirrel (Saimiri sciureus) monkeys due to Mycobacterium tuberculosis phage type B. Outbreak in a primate colony.* J Med Primatol, 1981. 10(6): p. 302-11.
7. Panarella, M. L. and R. S. Bimes, *A naturally occurring outbreak of tuberculosis in a group of imported cynomolgus monkeys (Macaca fascicularis).* J Am Assoc Lab Anim Sci, 2010. 49(2): p. 221-5.
8. Payne, K. S., et al., *Mycobacterium tuberculosis infection in a closed colony of rhesus macaques (Macaca mulatta).* J Am Assoc Lab Anim Sci, 2011. 50(1): p. 105-8.
9. Ward, G. S., et al., *Use of streptomycin and isoniazid during a tuberculosis epizootic in a rhesus and cynomolgus breeding colony.* Lab Anim Sci, 1985. 35(4): p. 395-9.
10. Zumpe, D., M. S. Silberman, and R. P. Michael, *Unusual outbreak of tuberculosis due to Mycobacterium bovis in a closed colony of rhesus monkeys (Macaca mulatta).* Lab Anim Sci, 1980. 30(2 Pt 1): p. 237-40.
11. Sedgwick, C., J. Parcher, and R. Durham, *Atypical mycobacterial infection in the pig-tailed Macaque (Macaca nemestrina).* J Am Vet Med Assoc, 1970. 157(5): p. 724-5.
12. Snyder, S. B. and J. G. Fox, *Tuberculin testing in rhesus monkeys (Macaca mulatta): a comparative study using experimentally sensitized animals.* Lab Anim Sci, 1973. 23(4): p. 515-21.
13. Goodwin, B. T., C. P. Jerome, and B. C. Bullock, *Unusual lesion morphology and skin test reaction for Mycobacterium avium complex in macaques.* Lab Anim Sci, 1988. 38(1): p. 20-4.
14. Capuano, S. V., 3rd, et al., *Experimental Mycobacterium tuberculosis infection of cynomolgus macaques closely resembles the various manifestations of human M. tuberculosis infection.* Infect Immun, 2003. 71(10): p. 5831-44.
15. Flynn, J. L., et al., *Non-human primates: a model for tuberculosis research.* Tuberculosis (Edinb), 2003. 83(1-3): p. 116-8.
16. Corcoran, K. D. and G. P. Jaax, *An attempt to predict anergy in tuberculosis suspect cynomolgus monkeys.* Lab Anim Sci, 1991. 41(1): p. 57-62.
17. Gibson, J. P., M. W. Rohovsky, and J. W. Newberne, *Modification of the tuberculin response of rhesus monkeys by isoniazid therapy.* Lab Anim Sci, 1971. 21(1): p. 62-6.
18. Staley, E. C., et al., *Evaluation of tuberculin testing and measles prophylaxis procedures used in rhesus macaque quarantine/conditioning protocols.* Lab Anim Sci, 1995. 45(2): p. 125-30.
19. Garcia, M. A., et al., *Diagnosis of tuberculosis in macaques, using whole-blood in vitro interferon-gamma (PRIMAGAM) testing.* Comp Med, 2004. 54(1): p. 86-92.
20. Lyashchenko, K. P., et al., *PrimaTB STAT-PAK assay, a novel, rapid lateral-flow test for tuberculosis in nonhuman primates.* Clin Vaccine Immunol, 2007. 14(9): p. 1158-64.
21. Vervenne, R. A., et al., *TB diagnosis in non-human primates: comparison of two interferon-gamma assays and the skin test for identification of Mycobacterium tuberculosis infection.* Vet Immunol Immunopathol, 2004. 100(1-2): p. 61-71.
22. Bailey, C. and K. Mansfield, *Emerging and reemerging infectious diseases of nonhuman primates in the laboratory setting.* Vet Pathol, 2010. 47(3): p. 462-81.
23. Brusasca, P. N., et al., *Antigen recognition by serum antibodies in non-human primates experimentally infected with Mycobacterium tuberculosis.* Comp Med, 2003. 53(2): p. 165-72.
24. Min, F., et al., *Serum antibody responses to 10 Mycobacterium tuberculosis proteins, purified protein derivative, and old tuberculin in natural and experimental tuberculosis in rhesus monkeys. Clin Vaccine Immunol, 2011. 18(12): p. 2154-60.
25. Weibrecht, I., et al., *Proximity ligation assays: a recent addition to the proteomics toolbox.* Expert Rev Proteomics, 2010. 7(3): p. 401-9.
26. Cole, S. T., et al., *Deciphering the biology of Mycobacterium tuberculosis from the complete genome sequence.* Nature, 1998. 393(6685): p. 537-44.
27. Nahtman, T., et al., *Validation of peptide epitope microarray experiments and extraction of quality data.* J Immunol Methods, 2007. 328(1-2): p. 1-13.

The invention claimed is:

1. An immunoassay device comprising a capture reagent immobilized on a surface of the device, said capture reagent comprising base peptide SEQ ID NO:139 and up to five amino acids on either or both of the amino- or carboxy-terminus of the base peptide.

2. The immunoassay device of claim 1, wherein said device comprises at least one additional capture reagents comprising a peptide selected from the group consisting of SEQ ID NOs.141, 145, 147, 98 and 56.

* * * * *